(12) United States Patent
Allen et al.

(10) Patent No.: US 9,328,134 B2
(45) Date of Patent: May 3, 2016

(54) CARBOHYDRATE PHOSPHONATE DERIVATIVES AS MODULATORS OF GLYCOSYLATION

(71) Applicant: AMGEN INC., Thousand Oaks, CA (US)

(72) Inventors: John Gordon Allen, Thousand Oaks, CA (US); Christopher H. Fotsch, Thousand Oaks, CA (US); Michael J. Frohn, Thousand Oaks, CA (US); John Douglas McCarter, Ventura, CA (US); Mirna Mujacic, Seattle, WA (US); Alexander J. Pickrell, Westlake Village, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/767,737

(22) PCT Filed: Feb. 20, 2014

(86) PCT No.: PCT/US2014/017271
§ 371 (c)(1),
(2) Date: Aug. 13, 2015

(87) PCT Pub. No.: WO2014/130613
PCT Pub. Date: Aug. 28, 2014

(65) Prior Publication Data
US 2015/0376221 A1 Dec. 31, 2015

Related U.S. Application Data

(60) Provisional application No. 61/768,175, filed on Feb. 22, 2013.

(51) Int. Cl.
| | | |
|---|---|---|
| C07D 309/10 | (2006.01) | |
| C07D 309/14 | (2006.01) | |
| C07H 7/02 | (2006.01) | |
| C07K 16/28 | (2006.01) | |
| C12N 5/073 | (2010.01) | |

(52) U.S. Cl.
CPC ............... *C07H 7/02* (2013.01); *C07D 309/10* (2013.01); *C07D 309/14* (2013.01); *C07K 16/2875* (2013.01); *C12N 5/0603* (2013.01); *C07K 2317/14* (2013.01); *C07K 2317/41* (2013.01); *C12N 2501/999* (2013.01); *C12N 2510/00* (2013.01)

(58) Field of Classification Search
CPC ...... C07D 309/10; C07D 309/14; C07H 7/02; C07K 16/2875; C07K 2317/14; C07K 2317/41; C12N 2501/999; C12N 2510/00; C12N 5/0603
See application file for complete search history.

(56) References Cited

U.S. PATENT DOCUMENTS

| | | | |
|---|---|---|---|
| 7,214,775 B2 | 5/2007 | Hanai et al. | |
| 7,708,992 B2 | 5/2010 | Hanai et al. | |
| 8,163,551 B2 | 4/2012 | Alley et al. | |
| 8,993,326 B2 | 3/2015 | Alley et al. | |

FOREIGN PATENT DOCUMENTS

| | | |
|---|---|---|
| WO | 92/19632 A1 | 11/1992 |
| WO | 2006/120576 A2 | 11/2006 |
| WO | 2009/135181 A2 | 11/2009 |
| WO | 2010/141855 A1 | 12/2010 |
| WO | 2012/019165 A2 | 2/2012 |
| WO | 2014/031875 A1 | 2/2014 |

OTHER PUBLICATIONS

International Search Report for parent PCT Application No. PCT/US2014/017271, mailed on May 19, 2014.
International Preliminary Report on Patentability and Written Opinion for parent PCT Application No. PCT/US2014/017271 dated Aug. 25, 2015.
Lin, Y-N. et al., "Chemoenzymatic Synthesis of CDP-L-Fucose Derivatives as Potent and Selective [alpha]-1,3-Fucosyltransferase Inhibitors", Advanced Synthesis & Catalysis, vol. 354(9), pp. 1750-1758 (2012).
Rillahan, C. D. et al., "High-Throughput Screening for Inhibitors of Sialyl- and Fucosyltransfcrascs", Angewandte Chemie International Edition, vol. 50(52), pp. 12534-12537 (2011).
Winterbourne, D. J. et al., "2-Deoxy-2-fluoro-L-fucose and its Effect on L-[1-$^{14}$C]Fucose Utilization in Mammalian Cells", Biochemical and Biophysical Research Communications, vol. 87(4), pp. 989-992 (1979).
Rillahan, C. D. et al., "Global Metabolic Inhibitors of Sialyl- and Fucosyl transferases remodesl the Glycome", Nature Chemical Biology, vol. 8, pp. 661-668 (2012).
Okeley, N. M. et al., "Metabolic Engineering of Monoclonal Antibody Carbohydrates for Antibody-Drug Conjugation", Bioconjugate Chemistry, vol. 24, pp. 1650-1655 (2014).
Pouilly, S. et al., "Evaluation of Analogues of GalNAc as Substrates for Enzymes of the Mammalian GalNAc Salvage Pathway", ACS Chemical Biology, no volume or pages provided (2012).
Arjona, O. et al., "Synthesis and Conformational and Biological Aspects of Carbasugars", Chem Reviews, vol. 107, pp. 1919-2036 (2007).

(Continued)

*Primary Examiner* — Valerie Rodriguez-Garcia
(74) *Attorney, Agent, or Firm* — Bernard P. Friedrichsen

(57) ABSTRACT

Compounds of Formula (I) are useful as modulators of glycosylation. Compounds of Formula (I) have the following structure: (I) and the definitions of the other variables are provided herein.

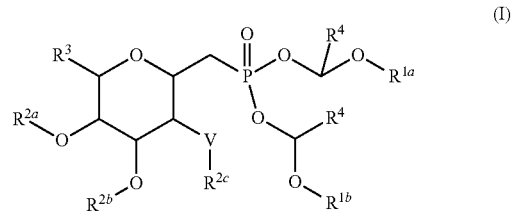

38 Claims, 3 Drawing Sheets

(56) References Cited

OTHER PUBLICATIONS

Ihara, H. et al., "Crystal Structure of Mammalian α1,6-Fucosyltransferase, FUT8", Glucobiology, vol. 17(5), pp. 455-466 (2007).

Somers, W. S. et al., "GDP-fucose Synthetase from *Escherichia coli*: Structure of a Unique member of the Short-Chain Dehydrogenase/Reductase Family that Catalyzes Two Distinct Reactions at the Same Active Site", Structure, vol. 6(12), pp. 1601-1612 (1998).

Ernst, B. et al., "From Carbohydrate Leads to Glycomimetic Drugs", Nature Reviews Drug Discovery, vol. 8, pp. 661-677 (2009).

King, J. D. et al., "The Structural Basis for Catalytic Function of GMD and RMD, Two Closely Related Enzymes from the GDP-D-rhamnose Biosynthesis Pathway", FEBS Journal, vol. 276, pp. 2686-2700 (2009).

Rosano, C. et al., "Quarternary Assembly and Crystal Structure of GDP-D-mannose 4,6 Dehydratase from *Paramecium bursaria Chlorella* Virus", Biochemical and Biophysical Research Communications, vol. 339, pp. 191-195 (2006).

Somoza, J. R. et al., "Structural and Kinetic Analysis of *Escherichia coli* GDP-mannose 4,6 Dehydratase Provides Insights into the Enzyme's Catalytic Mechanism and regulation by GDP-fucose", Structure, vol. 8(2), pp. 123-135 (2000).

Webb, N. A. et al., "Crystal Structure of a Tetrameric GDP-D-mannose 4, 6-Dehydratase from a bacterial GDP-d-rhamnose Biosynthetic Pathway", Protein Science, vol. 13, pp. 529-539 (2004).

Mulichak, A. M. et al., "Structure of the MUR1 GDP-Mannose 4,6-Dehydratase from *Arabidopsis thaliana*: Implications for Ligand Binding and Specificity", Biochemistry, vol. 41, pp. 15578-15589 (2002).

Gloster, T. N. et al., "Developing Inhibitors of Glycan Processing Enzymes as Tools for Enabling Glycobiology", Nature Chemical Biology, vol. 8, pp. 683-694 (2012).

Junttila, T. T. et al., "Superior In vivo Efficacy of Afucosylated Trastuzumab in the Treatment of HER2-Amplified Breast Cancer", Cancer Research, vol. 70(11), pp. 4481-4489 (2010).

Chartraim, M. et al., "Development and Production of Commercial Therapeutic Monoclonal Antibodies in Mammalian Cell Expression Systems: An Overview of the Current Upstream Technologies", Current Pharmaceutical Biotechnology, vol. 9, pp. 447-467 (2008).

Becker, D. et al., "Fucose: Biosynthesis and Biological Function in Mammals", Glycobiology, vol. 13(7), pp. 41R-53R (2003).

Compain, P. et al., "Carbohydrate Mimetifs-Based Glycosyltransferase Inhibitors", Bioorganic & Medicinal Chemistry, vol. 9, pp. 3077-3092 (2001).

Kajimoto, T. et al., "Synthesis of Glycosyltransferase Inhibitors", Synthesis, vol. 19, pp. 3179-3210 (2009).

Kavanagh, K. L. et al., "The SDR Superfamily: Functional and Structural Diversity Within a Family of Metabolic and Regulatory Enzymes" Cellular and Molecular Life Sciences, vol. 65, pp. 3895-3906 (2008).

Alley, S. C. et al., "SEA Technology: A Novel Strategy for Enhance Antibody Effector Function", AACR, Apr. 17-21, 2010.

Zandberg, W. F. et al., "Metabolic Inhibition of Sialyl-Lewis X Biosynthesis by 5-Thiofucose Remodels the Cell Surface and Impairs Selectin-Mediated Cell Adhesion", Journal of Biological Chemistry, vol. 287(47), pp. 40021-40030 (2012).

Okeley, N. M. et al., "Development of Orally Active Inhibitors of Protein and Cellular Fucosylation", PNAS Early Edition, pp. 1-6 (2013).

Bansal, R. et al., "Synthesis of Trifluoromethyl Analogue of L-Fucose and 6-Deoxy-D-altrose", Journal of the Chemical Society, Chemical Communications, pp. 796-798 (1991).

Belcher, J. D. et al., "The Fucosylation Inhibitor, 2-Fluorofucose, Inhibits Vaso-Occlusion, Leukocytge-Endothelium Interactions and NF-κB Activation in Transgenic Sickle Mice", PLoS One, Feb. 23, 2015, pp. 1-11 (2015).

Li, J. et al., "Inhibition of Fucosylation Reshapes Inflammatory Macrophages and Suppresses Type II Collagen-Induced Arthritis", Arthritis and Rheumatology, vol. 66(9), pp. 2368-2379 (2014).

CARBOHYDRATE PHOSPHONATE DERIVATIVES AS MODULATORS OF GLYCOSYLATION

CROSS REFERENCES TO RELATED APPLICATIONS

This application is a national stage application under 35 §371 of International Application No. PCT/US2014/017271, having an international filing date of Feb. 20, 2014, which claims the benefit of U.S. Provisional Application No. 61/768,175, filed on Feb. 22, 2013, which is hereby incorporated by reference in its entirety and for all purposes as if fully set forth herein.

FIELD OF THE INVENTION

The present invention relates to carbohydrate derivatives that are useful for modifying carbohydrate incorporation into proteins such as antibodies during the production of such proteins in eukaryotic cell cultures. More specifically, the invention relates to compounds that are useful in inhibiting fucosylation of proteins such as antibodies during production from eukaryotic cell cultures. The invention also relates to carbohydrate phosphonate derivatives that are useful in modulating the amount of mannose incorporation into proteins during production from eukaryotic cell lines.

BACKGROUND OF THE INVENTION

Therapeutic antibodies with reduced levels of fucosylation or absent fucosylation have been shown to exhibit enhanced antibody-dependent cellular cytotoxicity (ADCC) due to increased binding to FcγR III. Increased ADCC has been associated with improved in vivo efficacy in animal models and in the clinic. Other therapeutic antibodies dependent on ADCC for efficacy are also expected to benefit from reduced levels of fucosylation or absent fucosylation. In addition, fucosylation levels of antibodies are an important product attribute that is desirable to match during the production of bio similar products.

Antibody fucosylation may be reduced by use of cell lines in which one or more of the key enzymes involved in protein fucosylation (GDP-mannose dehydratase (GMD), GDP-fucose synthase (GFS), or alpha-(1,6)-fucosytransferase 8 (FUT8) are either genetically knocked out or through chemical inhibition or inactivation of these enzymes. The use of knockout cell lines often requires optimization of manufacturing processes in these cell lines. Even so, cell growth characteristics, product yields, and product attribute qualities may be sub-optimal. In contrast, a small molecule inhibitor or inactivator of enzymes involved in fucosylation may be used to reduce antibody fucosylation without resort to use of engineered cell lines. The alpha-mannosidase inhibitor kifunsenine reduces antibody fucosylation in cell culture but increases high mannose glycan structures resulting in faster clearance of the antibody.

Described herein are novel small molecules designed to reduce antibody fucosylation efficiently without undesirable effects on cell growth or viability, modification of high mannose structures, or, in some cases, being incorporated into antibody glycans.

SUMMARY OF THE INVENTION

In one embodiment, the invention provides a compound of Formula I:

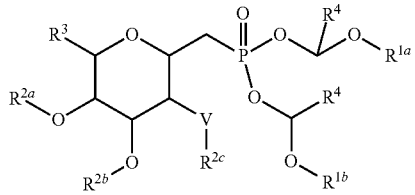

wherein V is O or NH; and further wherein the compound of Formula I is selected from a compound of Formula IA, IB, or IC:

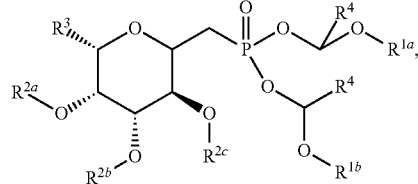

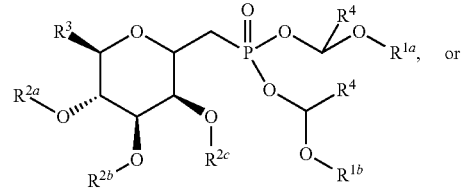

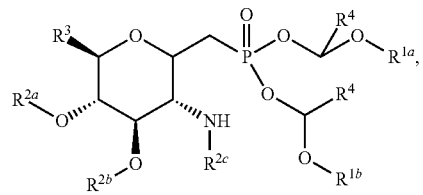

wherein:

$R^{1a}$ and $R^{1b}$ are independently selected from —C(=O)—$(C_1$-$C_{10}$ alkyl), or —C(=O)—$(C_6$-$C_{10}$ aryl);

$R^{2a}$, $R^{2b}$, and $R^{2a}$ are —C(=O)CH$_3$;

$R^3$ is —CH$_2$O—C(=O)CH$_3$ if the compound of Formula I is a compound of Formula IB;

$R^3$ is selected from $(C_1$-$C_6)$alkyl, perhalo$(C_1$-$C_6)$alkyl, halo$(C_1$-$C_6)$alkyl, —CH$_2$O—C(=O)—$(C_1$-$C_6$ alkyl), or $(C_2$-$C_6)$alkynyl; and $R^4$ is independently selected from H or —CH$_3$.

In some embodiments, the compound of Formula I is a compound of Formula IA. In other embodiments, the compound of Formula I is a compound of Formula IB. In other embodiments, the compound of Formula I is a compound of Formula IC.

In some embodiments, the compound is a compound of Formula IA'

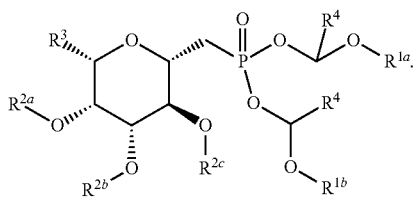

In some embodiments, the compound is a compound of Formula IA″

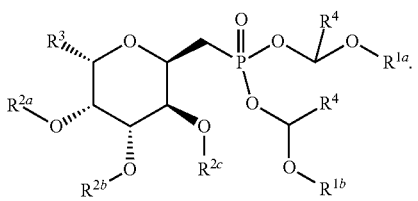

In some embodiments, the compound is a compound of Formula IB′

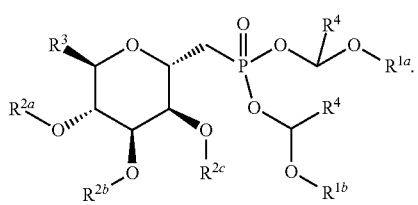

In some embodiments, the compound is a compound of Formula IC′

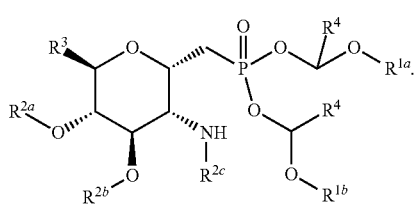

In some embodiments, the compound is

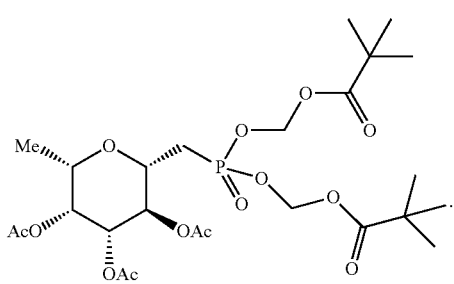 [SMILES: CC(=O)O[C@@H]1[C@H](OC(C)=O)[C@H](C)O[C@H](CP(=O)(OCOC(=O)C(C)(C)C)OCOC(=O)C(C)(C)C)[C@H]1OC(C)=O]

In some embodiments, the compound is

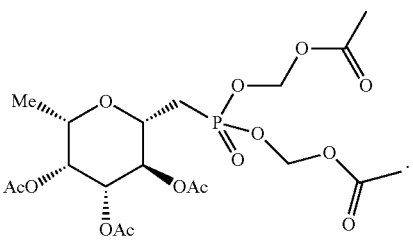 [SMILES: CC(=O)OCOP(=O)(C[C@H]1O[C@@H](C)[C@@H](OC(C)=O)[C@@H](OC(C)=O)[C@@H]1OC(C)=O)OCOC(C)=O]

In some embodiments, the compound is

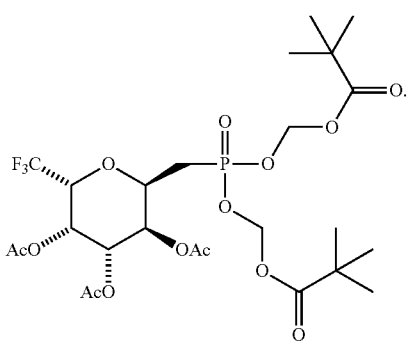 [SMILES: CC(=O)O[C@H]1[C@H](OC(C)=O)[C@H](CP(=O)(OCOC(=O)C(C)(C)C)OCOC(=O)C(C)(C)C)O[C@@H](C(F)(F)F)[C@H]1OC(C)=O]

In some embodiments, the compound is

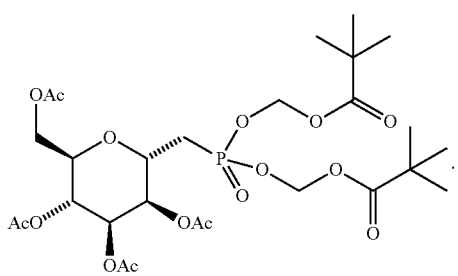 [SMILES: CC(=O)OC[C@H]1O[C@H](CP(=O)(OCOC(=O)C(C)(C)C)OCOC(=O)C(C)(C)C)[C@@H](OC(C)=O)[C@@H](OC(C)=O)[C@@H]1OC(C)=O]

In some embodiments, the compound is

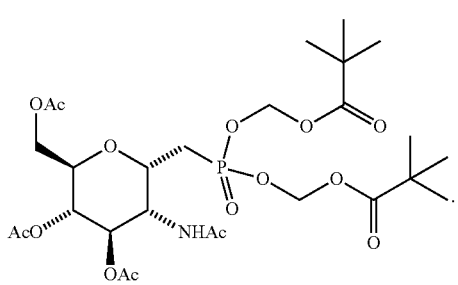 [SMILES: CC(=O)N[C@@H]1[C@@H](OC(C)=O)[C@H](OC(C)=O)[C@@H](COC(C)=O)O[C@@H]1CP(=O)(OCOC(=O)C(C)(C)C)OCOC(=O)C(C)(C)C]

In some embodiments of the compounds of Formula I, $R^3$ is selected from $(C_1-C_6)$alkyl, perhalo$(C_1-C_6)$alkyl, or —CH$_2$O—C(=O)—($C_1$-$C_6$ alkyl). In some embodiments, $R^3$ is selected from CF$_3$, CH$_3$, or —CH$_2$O—C(=O)CH$_3$. In some such embodiments, $R^3$ is CH$_3$ or CF$_3$. In some such embodiments, $R^3$ is CH$_3$ whereas in other such embodiments, $R^3$ is CF$_3$. In other embodiments, $R^3$ is —CH$_2$O—C(=O)—($C_1$-$C_6$ alkyl) and in some such embodiments is —CH$_2$O—C(=O)CH$_3$.

In some embodiments of the compounds of Formula I, $R^{1a}$ and $R^{1b}$ are —C(=O)—($C_1$-$C_6$ alkyl). In some such embodiments, $R^{1a}$ and $R^{1b}$ are selected from —C(=O)$CH_3$ or —C(=O)—C($CH_3$)$_3$. In some embodiments, $R^{1a}$ and $R^{1b}$ are both —C(=O)—($C_1$-$C_6$ alkyl), and the —C(=O)—($C_1$-$C_6$ alkyl) is independently selected from —C(=O)$CH_3$, —C(=O)$CH_2CH_3$, —C(=O)$CH_2CH_2CH_3$, —C(=O)$CH_2CH_2CH_2CH_3$, —C(=O)CH($CH_3$)$_2$, —C(=O)C($CH_3$)$_3$, or —C(=O)CH($CH_3$)($CH_2CH_3$). In some embodiments, $R^{1a}$ and $R^{1b}$ are both —C(=O)$CH_3$, whereas in other embodiments, $R^{1a}$ and $R^{1b}$ are both —C(=O)C($CH_3$)$_3$. In still other embodiments, $R^{1a}$ and $R^{1b}$ are both —C(=O)—($C_6$-$C_{10}$ aryl) and the —C(=O)—($C_6$-$C_{10}$ aryl) is —C(=O)-phenyl.

In some embodiments of the compounds of Formula I, $R^4$ is H in both instances, whereas in other embodiments of the compounds of Formula I, $R^4$ is $CH_3$ in both instances.

In yet other embodiments, the invention includes a method for culturing eukaryotic cells, the method typically includes culturing the cells in a cell culture media that includes the compound of any of the embodiments.

In still another embodiment, the invention includes a method for preparing a protein such as one having modified glycan content. Such methods typically include culturing eukaryotic host cells in a cell culture media that includes a compound of any one of the embodiments, and isolating the protein.

The methods of the invention may be used to produce various proteins. For example, in some embodiments, the protein is a therapeutic protein. In some such embodiments, the protein may be fully human. In other embodiments, the protein may be an antibody. In some such embodiments, an antibody produced using the methods of the invention may be a fully human antibody, a chimeric antibody, or a humanized antibody. For example, as shown in the examples, the methods using the compounds of any of the embodiments may be used to produce an anti TRAIL antibody.

Various eukaryotic cells may be used in accordance with the methods of the invention. For example, in some embodiments, the cells may be mammalian cells such as, in some embodiments, Chinese Hamster Ovary (CHO) cells. In other embodiments, yeast cells may be used.

The compounds of the invention may be present in the cell culture media at various concentrations. In some embodiments, for example, the compound may be present in the cell culture media at a concentration that ranges from 1 mM to 100 nM. In some such embodiments, the concentration ranges from 500 uM to 1 uM. In still other such embodiments, the concentration ranges from 320 uM to 5 uM. In yet other such embodiments, the concentration ranges from 200 uM to 50 uM. In any such embodiments, the compound may be added to the cell culture media in a single dose, once a day, twice a day, three times a day, four times a day, once every two days, once every three days, or continuously. Adding the compound to the cell culture media on a daily basis has been found to be highly advantageous.

Other objects, features and advantages of the invention will become apparent to those skilled in the art from the following description and claims.

DETAILED DESCRIPTION OF THE INVENTION

Figure 1:
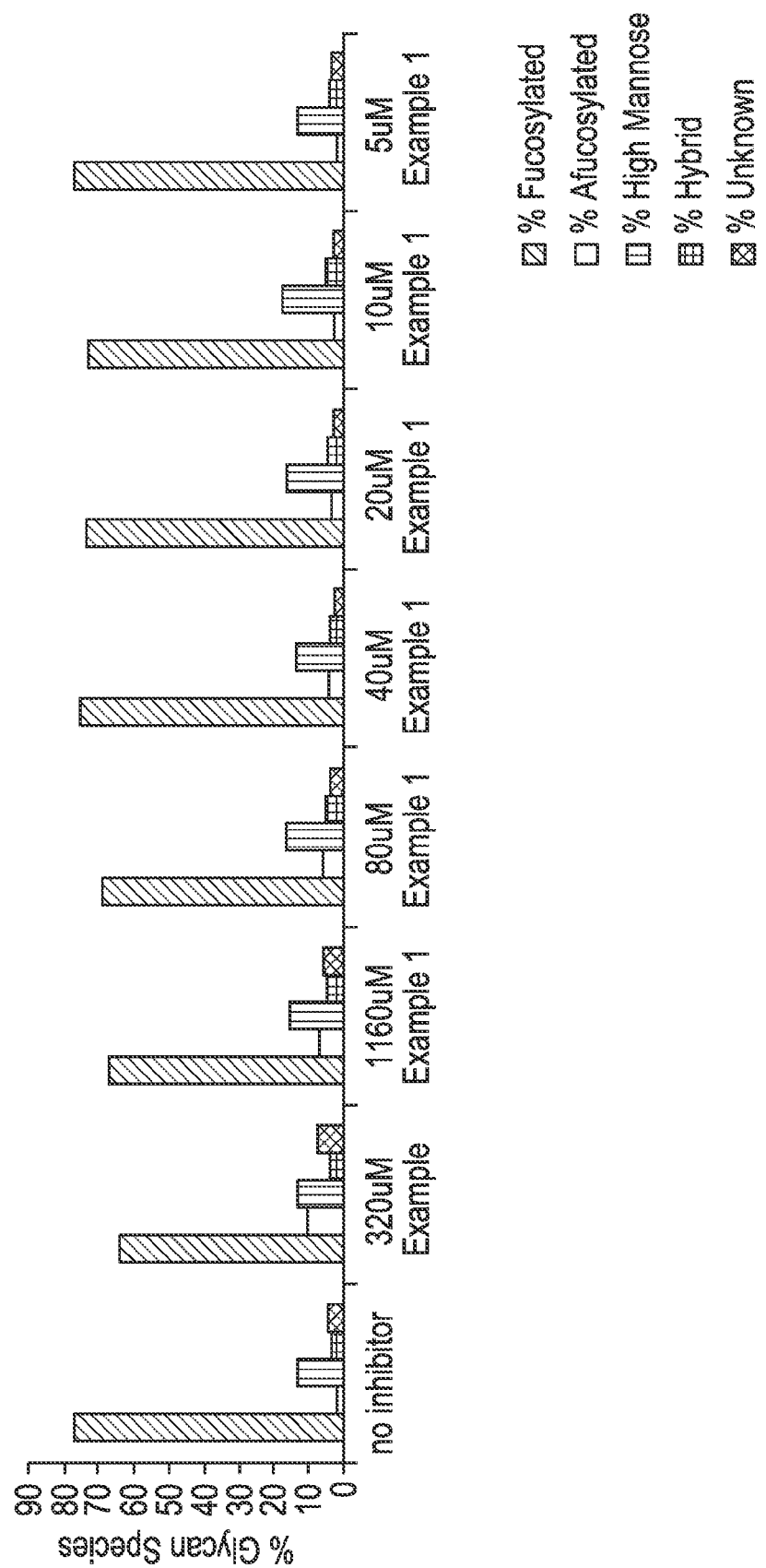
FIG. 1. is a graph comparing the glycan profile of anti-Trail IgG1 produced in the absence of Example 1 and in the presence of the Example 1 at various concentrations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. As noted above, various compounds of the invention may contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula. The same is true with respect to stereoisomers unless a specific stereochemistry is shown or noted. For example, a compound of a specific formula includes all stereoisomers or mixtures thereof. Similarly, a pharmaceutically acceptable salt of the compound includes pharmaceutically acceptable salts of all individual stereoisomers or mixtures thereof.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, research reagents, e.g., assay reagents such as the $^{14}C$ thymidine incorporation assay, and diagnostic agents, e.g., in vivo imaging agents. All isotopic variations of the compounds of the invention, whether radioactive or not, are intended to be encompassed within the scope of the invention. For example, if a variable is said to be H or —H, this means that the variable may also be deuterium (D) or tritium (T).

As used herein, the terms "comprising" and "including" and other forms of these words are used herein in their open, non-limiting sense. For example, if a composition is said to comprise A, B, and C, then A, B, and C are in the composition, but D, E, and/or F may be in the composition as well.

The term "alkyl" refers to a saturated, branched, straight-chain, or cyclic monovalent hydrocarbon group or combination thereof derived by the removal of one hydrogen atom from a single carbon atom of a parent alkane or cycloalkane. Typical alkyl groups include, but are not limited to, methyl (—$CH_3$); ethyl (—$CH_2CH_3$); propyls such as propan-1-yl (—$CH_2CH_2CH_3$), propan-2-yl (—$CH(CH_2)_2$), and cyclopropyl; and butyls such as butan-1-yl (—$CH_2CH_2CH_2CH_3$), butan-2-yl, —$CH(CH_3)CH_2CH_3$ 2-methyl-propan-1-yl (—$CH_2CH(CH_3)_2$), tert-butyl (—$C(CH_3)_3$), methylcyclopropyl, and cyclobutyl, and the like. In certain embodiments, an alkyl group comprises 1 to 10 carbon atoms. In some embodiments, alkyl groups include 1 to 6 carbon atoms whereas in other embodiments, alkyl groups include 1 to 4 or 1 to 3 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 10 carbon atoms may be referred to as a —($C_1$-$C_{10}$)alkyl or —($C_1$-$C_{10}$) alkyl group, an alkyl group having 1 to 6 carbon atoms may be referred to as a —($C_1$-$C_6$)alkyl or —($C_1$-$C_6$) alkyl group, an alkyl group having 1 to 4 carbon atoms may be referred to as a —($C_1$-$C_4$)alkyl or —($C_1$-$C_4$) alkyl, and an alkyl group having 1 to 3 carbon atoms may be referred to as a —($C_1$-$C_3$)alkyl or —($C_1$-$C_3$) alkyl. The same designation system applies to alkyl groups with different numbers of carbon atoms. Alkyl groups may be substituted or may be unsubstituted. In some embodiments, alkyl groups are unsubstituted. In other embodiments, an alkyl group may be substituted with one or more substituents. For example, in some embodiments, an alkyl group may be substituted with 1, 2 or 3 substituents whereas in another embodiment, an alkyl group may, where permitted by valence, be substituted with 1 to 5 substituents.

The term "cycloalkyl" refers to a saturated cyclic alkyl group derived by the removal of one hydrogen atom from a single carbon atom of a parent cycloalkane. Typical cycloalkyl groups include, but are not limited to, cyclopropyl, cyclobutyl, cyclopentyl, cyclohexyl, methylcyclopropyl, methylcyclobutyl, and the like. In certain embodiments, the cycloalkyl group can be $C_3$-$C_6$ cycloalkyl, such as, for example, $C_3$-$C_5$ cycloalkyl. Cycloalkyl groups may be substituted or unsubstituted.

The term "halo" or "halogen" refers to a fluoro (—F), chloro (—Cl), bromo (—Br), or iodo (—I) group.

The term "haloalkyl" refers to an alkyl group as defined above in which at least one hydrogen atom is replaced with a halogen. Thus, the term "haloalkyl" includes "monohaloalkyl" (an alkyl substituted with one halogen atom), "dihaloalkyl" (an alkyl substituted with two halogen atoms which may be the same or different), and "trihaloalkyl" (an alkyl substituted with three halogen atoms which may be the same or different). The term "polyhaloalkyl" refers to an alkyl group that is substituted with two or more halogen atoms. The term "perhaloalkyl" means, unless otherwise stated, an alkyl group in which each of the hydrogen atoms is replaced with a halogen atom. For example, the term "perhaloalkyl", includes, but is not limited to, trifluoromethyl (—$CF_3$), pentachloroethyl, 1,1,1-trifluoro-2-bromo-2-chloroethyl, and the like.

The term "aryl" means, unless otherwise stated, a polyunsaturated, aromatic, carbocyclic hydrocarbon substituent which can be a single ring or multiple rings (up to two rings) which are fused together or linked covalently. Typically an aryl group refers to an aromatic group that includes from 6-12 or 6-10 ring members such that it is a ($C_6$-$C_{12}$)aryl or a ($C_6$-$C_{10}$)aryl group. Aryl groups may be substituted or unsubstituted and include such groups as phenyl, naphthyl, biphenyl, and the like. In some preferred embodiments, aryl refers to phenyl.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, alternating flow bioreactors, roller bottles, shake flasks, or stirred tank bioreactors, with or without microcarriers, can be used. In one embodiment 500 L to 2000 L bioreactors are used. In one embodiment, 1000 L to 2000 L bioreactors are used.

As used herein, the terms "medium," "cell culture medium" and "culture medium" are used interchangeably and mean a solution containing nutrients that nourish growing cells. In certain embodiments, a culture medium is useful for growing mammalian cells. Cell culture media formulations are well known in the art; typically, a culture medium provides essential and non-essential amino acids, vitamins, energy sources, lipids, and trace elements required by the cell for minimal growth and/or survival, as well as buffers, and salts. A culture medium may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source; as described herein, cell-cycle inhibitors can be added to a culture medium. In certain embodiments, a medium is advantageously formulated to a pH and salt concentration optimal for cell survival and proliferation. In certain embodiments, the medium is a culture medium (for example, a feed medium) that is added after the beginning of the cell culture. In certain embodiments, the cell culture medium is a mixture of a starting nutrient solution and any culture medium that is added after the beginning of the cell culture.

"Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

Eukaryotic cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J. Biol Chem* 263:6352-6362; McKinnon et al. (1991), *J Mol Endocrinol* 6:231-239; Wood et al. (1990), *J. Immunol.* 145:3011-3016). The dihydrofolate reductase (DHFR)-deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments

The embodiments listed below are presented in numerical order for easy and convenience of reference. The listing of such embodiments Is not meant to limit the invention as described above.

1. In a first embodiment, the invention provides a compound of Formula I:

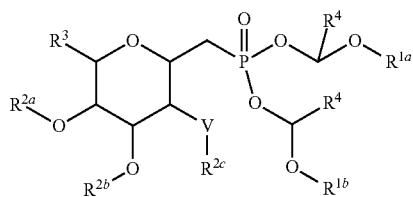

wherein V is O or NH; and further wherein the compound of Formula I is selected from a compound of Formula IA, IB, or IC:

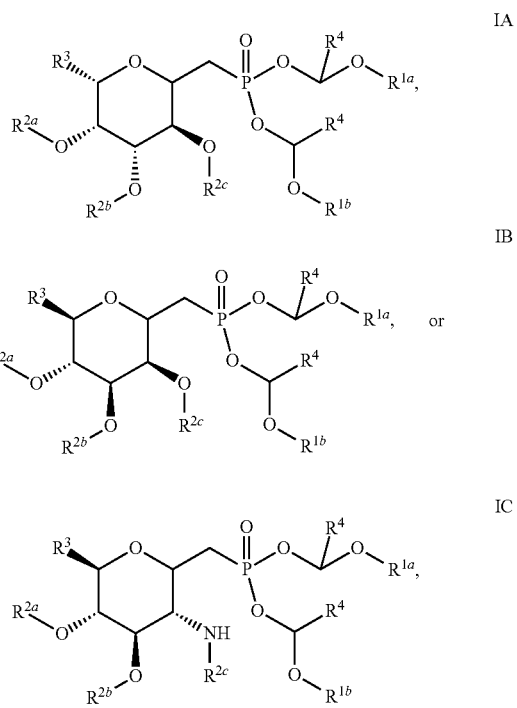

wherein:

$R^{1a}$ and $R^{1b}$ are independently selected from —C(=O)—($C_1$-$C_{10}$ alkyl), or —C(=O)—($C_6$-$C_{10}$ aryl);

$R^{2a}$, $R^{2b}$, and $R^{2c}$ are —C(=O)$CH_3$;

$R^3$ is —$CH_2$O—C(=O)$CH_3$ if the compound of Formula I is a compound of Formula IB;

$R^3$ is selected from ($C_1$-$C_6$)alkyl, perhalo($C_1$-$C_6$)alkyl, halo($C_1$-$C_6$)alkyl, —$CH_2$O—C(=O)—($C_1$-$C_6$ alkyl), or ($C_2$-$C_6$)alkynyl; and $R^4$ is independently selected from H or —$CH_3$.

2. The compound of embodiment 1, wherein the compound of Formula I is a compound of Formula IA.

3. The compound of embodiment 2, wherein the compound of Formula IA is a compound of Formula IA'

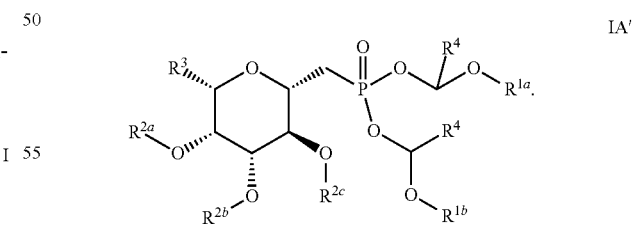

4. The compound of embodiment 3, wherein $R^3$ is $CH_3$ or $CF_3$.

5. The compound of embodiment 3 or embodiment 4, wherein $R^{1a}$ and $R^{1b}$ are —C(=O)—($C_1$-$C_6$ alkyl).

6. The compound of any one of embodiments 3-5, wherein $R^{1a}$ and $R^{1b}$ are selected from —C(=O)$CH_3$ or —C(=O)—C($CH_3$)$_3$.

7. The compound of embodiment 2, wherein the compound is

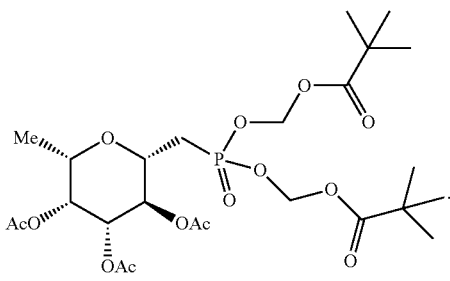 [SMILES: CC(=O)O[C@@H]1[C@H](OC(C)=O)[C@H](C)O[C@H](CP(=O)(OCOC(=O)C(C)(C)C)OCOC(=O)C(C)(C)C)[C@H]1OC(C)=O]

8. The compound of embodiment 2, wherein the compound is

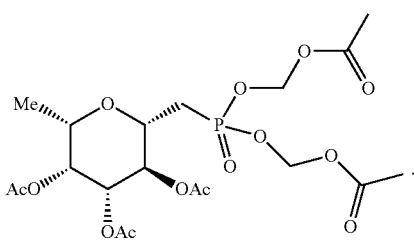 [SMILES: CC(=O)OCOP(=O)(C[C@H]1O[C@@H](C)[C@@H](OC(C)=O)[C@@H](OC(C)=O)[C@@H]1OC(C)=O)OCOC(C)=O]

9. The compound of embodiment 2, wherein the compound of Formula IA is a compound of Formula IA''

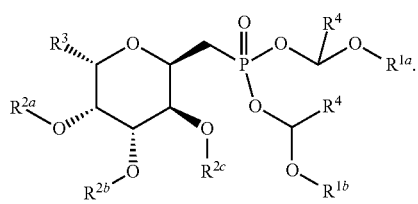

10. The compound of embodiment 9, wherein $R^3$ is $CF_3$.

11. The compound of embodiment 9 or embodiment 10, wherein $R^{1a}$ and $R^{1b}$ are —C(=O)—($C_1$-$C_6$ alkyl).

12. The compound of any one of embodiments 9-11, wherein $R^{1a}$ and $R^{1b}$ are selected from —C(=O)CH$_3$ or —C(=O)—C(CH$_3$)$_3$.

13. The compound of embodiment 2, wherein the compound is

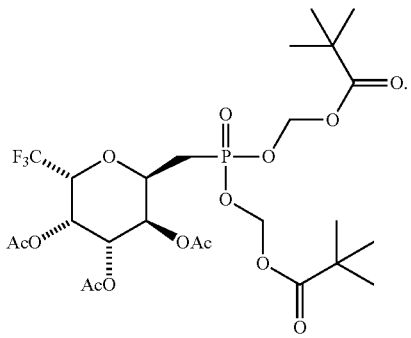 [SMILES: CC(=O)O[C@H]1[C@H](OC(C)=O)[C@H](CP(=O)(OCOC(=O)C(C)(C)C)OCOC(=O)C(C)(C)C)O[C@@H](C(F)(F)F)[C@H]1OC(C)=O]

14. The compound of embodiment 1, wherein the compound of Formula I is a compound of Formula IB.

15. The compound of embodiment 14, wherein the compound of Formula IB is a compound of Formula IB'

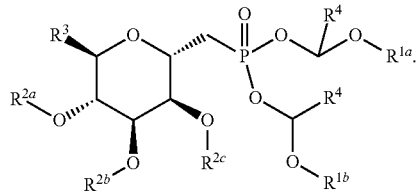

16. The compound of embodiment 14 or embodiment 15, wherein $R^{1a}$ and $R^{1b}$ are —C(=O)—($C_1$-$C_6$ alkyl).

17. The compound of any one of embodiments 14-16, wherein $R^{1a}$ and $R^{1b}$ are selected from —C(=O)CH$_3$ or —C(=O)—C(CH$_3$)$_3$.

18. The compound of embodiment 14, wherein the compound is

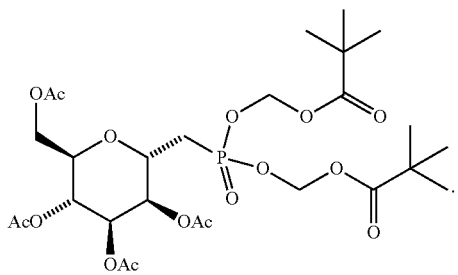 [SMILES: CC(=O)OC[C@H]1O[C@H](CP(=O)(OCOC(=O)C(C)(C)C)OCOC(=O)C(C)(C)C)[C@@H](OC(C)=O)[C@@H](OC(C)=O)[C@@H]1OC(C)=O]

19. The compound of embodiment 1, wherein the compound of Formula I is a compound of Formula IC.

20. The compound of embodiment 19, wherein the compound of Formula IC is a compound of Formula IC'

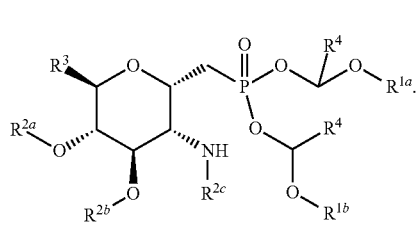

21. The compound of embodiment 19 or embodiment 20, wherein $R^3$ is $CH_3$ or $CF_3$.

22. The compound of embodiment 19 or embodiment 20, wherein $R^3$ is —CH$_2$O—C(=O)—($C_1$-$C_6$ alkyl).

23. The compound of embodiment 22, wherein $R^3$ is —CH$_2$O—C(=O)CH$_3$.

24. The compound of any one of embodiments 19-23, wherein $R^{1a}$ and $R^{1b}$ are —C(=O)—($C_1$-$C_6$ alkyl).

25. The compound of any one of embodiments 19-24, wherein $R^{1a}$ and $R^{1b}$ are selected from —C(=O)CH$_3$ or —C(=O)C(CH$_3$)$_3$.

26. The compound of embodiment 19, wherein the compound is

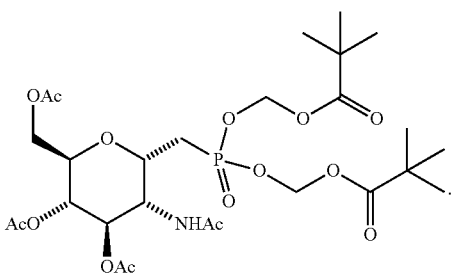 [SMILES: CC(=O)N[C@@H]1[C@@H](OC(C)=O)[C@H](OC(C)=O)[C@@H](COC(C)=O)O[C@@H]1CP(=O)(OCOC(=O)C(C)(C)C)OCOC(=O)C(C)(C)C]

27. The compound of embodiment 1, wherein $R^{1a}$ and $R^{1b}$ are both —C(=O)—($C_1$-$C_6$ alkyl), and further wherein the —C(=O)—($C_1$-$C_6$ alkyl) is independently selected from —C(=O)$CH_3$, —C(=O)$CH_2CH_3$, —C(=O)$CH_2CH_2CH_3$, —C(=O)$CH_2CH_2CH_2CH_3$, —C(=O)$CH(CH_3)_2$, —C(=O)$C(CH_3)_3$, or —C(=O)$CH(CH_3)(CH_2CH_3)$.

28. The compound of embodiment 1, wherein $R^{1a}$ and $R^{1b}$ are both —C(=O)$CH_3$.

29. The compound of embodiment 1, wherein $R^{1a}$ and $R^{1b}$ are both —C(=O)$C(CH_3)_3$.

30. The compound of embodiment 1, wherein $R^{1a}$ and $R^{1b}$ are both —C(=O)—($C_6$-$C_{10}$ aryl) and the —C(=O)—($C_6$-$C_{10}$ aryl) is —C(=O)-phenyl.

31. The compound of any one of embodiments 1, or 27-30, wherein $R^3$ is selected from ($C_1$-$C_6$)alkyl, perhalo($C_1$-$C_6$) alkyl, or —$CH_2$O—C(=O)—($C_1$-$C_6$ alkyl).

32. The compound of embodiment 31, wherein $R^3$ is selected from $CF_3$, $CH_3$, or —$CH_2$O—C(=O)$CH_3$.

33. The compound of any one of embodiments 1-6, 9-12, 14-17, 19-25, or 28-32, wherein $R^4$ is —H in both instances.

34. The compound of any one of embodiments 1-6, 9-12, 14-17, 19-25, or 28-32, wherein $R^4$ is —$CH_3$ in both instances.

35. In yet another embodiment, the invention provides a method for culturing eukaryotic cells, the method comprising: culturing the cells in a cell culture media, wherein the cell culture media comprises the compound of any one of embodiments 1-34. Various types of cell lines may be used in accordance with the invention. Examples of such cell lines, include, but are not limited to mammalian production cell lines. Cell lines such as various types of CHO cells (CHOK1, DG44, DXB11, CHO-s), HEK293, BHK, Perc6, Sp2/0, NS0, and the like are all nonlimiting examples of cell lines that may be used. In some examples, the cell line used in the methods of the invention is a cell that has been transfected with an expression vector.

36. In still another embodiment, the invention provides a method for preparing a protein having modified glycan content, the method comprising: culturing eukaryotic host cells in a cell culture media comprising the compound of any one of embodiments 1-34, and isolating the protein. In some embodiments, the protein produced by the methods of the invention is a recombinant protein. As will be readily apparent, a wide variety of proteins may be produced using the methods of the invention. Examples of some of these include, but are not limited to, therapeutic proteins, antibodies, BiTes, FC-fusion molecules, bispecific antibodies, antibody-drug conjugates, and the like.

37. The method of embodiment 36, wherein the protein is an antibody.

38. The method of embodiment 37, wherein the antibody is an anti TRAIL antibody.

39. The method of any one of embodiments 35-38, wherein the cells are mammalian cells.

40. The method of any one of embodiments 35-39, wherein the cells are CHO cells.

41. The method of any one of embodiments 35-38, wherein the cells are yeast cells.

42. The method of embodiment 35 or embodiment 36, wherein the concentration of the compound in the cell culture media ranges from 1 mM to 100 nM. In some such embodiments, the concentration ranges from 500 uM to 1 uM. In still other such embodiments, the concentration ranges from 320 uM to 5 uM. In yet other such embodiments, the concentration ranges from 200 uM to 50 uM. In any such embodiments, the compound may be added to the cell culture media in a single dose, once a day, twice a day, three times a day, four times a day, once every two days, once every three days, or continuously.

43. The method of any one of embodiments 35-42, wherein the compound is added to the cell culture media in a single dose.

44. The method of any one of embodiments 35-42, wherein the compound is added to the cell culture media once each day.

45. The method of any one of embodiments 35-42, wherein the compound is continuously added to the cell culture media.

46. In yet another embodiment, the invention provides a protein produced in accordance with the method of embodiment 36.

47. The protein of embodiment 46, wherein the protein is an antibody.

48. The protein of embodiment 46, wherein the protein is a therapeutic protein.

49. The protein of embodiment 48, wherein the therapeutic protein is fully human.

50. The method of embodiment 37, wherein the antibody is fully human.

51. The method of embodiment 37, wherein the antibody is chimeric.

52. The method of embodiment 37, wherein the antibody is humanized.

Methods for culturing cells to produce proteins are well known in the art. The cells used in the methods of the invention are typically, cells that express a recombinant protein. The compounds of any of the embodiments may be added to cell culture media to modify the proteins that would be produced by the cells in the absence of the compounds of the invention. These proteins thus have a modified glycan content meaning that the proteins include a different amount of, and/or type of, carbohydrate than they would if they were produced in cell culture media that did not include the compounds of the present invention. In addition to being useful for modifying proteins produced by cells, some of the compounds of Formula I are not expected to be incorporated into the protein.

The compounds of Formula IA are novel derivatives of fucose and have the stereochemistry associated with fucose. These compounds may be added to cell culture media to inhibit fucosylation in the proteins produced by cells. Thus, addition of compounds of Formula IA such as Example 1 to cell culture media results in proteins with reduced amounts of fucose compared to proteins produced in the absence of the compounds.

The compounds of Formula IB are novel derivatives of mannose and have the stereochemistry associated with mannose. These compounds may be added to cell culture media to decrease the amount of mannose incorporated into the proteins produced by cells. Thus, addition of compounds of Formula IB to cell culture media will be found to result in proteins with reduced amounts of mannose compared to proteins produced in the absence of the compounds.

The compounds of Formula IC are novel derivatives of N-acetylglucosamine and have the stereochemistry associated with N-acetylglucosamine. These compounds may be added to cell culture media to increase the amount of mannose in the proteins produced by cells. Thus, addition of compounds of Formula IC to cell culture media results in proteins with increased amounts of mannose compared to proteins produced in the absence of the compounds.

The disclosed methods are applicable to any method for growing cells including adherent culture or suspension cultures grown in stirred tank reactors (including traditional batch and fed-batch cell cultures, which may, but need not comprise a spin filter), perfusion systems (including alternating tangential flow ("ATF") cultures, acoustic perfusion systems, depth filter perfusion systems, and other systems), hollow fiber bioreactors (HFB, which in some cases may be employed in perfusion processes) as well as various other cell culture methods (see, e.g., Tao et al., (2003) Biotechnol. Bioeng. 82:751-65; Kuystermans & Al-Rubeai, (2011) "Bioreactor Systems for Producing Antibody from Mammalian Cells" in Antibody Expression and Production, Cell Engineering 7:25-52, Al-Rubeai (ed) Springer; Catapano et al., (2009) "Bioreactor Design and Scale-Up" in Cell and Tissue Reaction Engineering: Principles and Practice, Eibl et al. (eds) Springer-Verlag, incorporated herein by reference in their entireties).

Some embodiments of the present inventive methods further comprise a step of harvesting a recombinant protein produced by the cell culture. In some such embodiments, the recombinant protein produced by the cell culture is purified and formulated in a pharmaceutically acceptable formulation.

The methods of the invention can be used to culture cells that express recombinant proteins of interest. The expressed recombinant proteins may be secreted into the culture medium from which they can be recovered and/or collected. In addition, the proteins can be purified, or partially purified, from such culture or component (e.g., from culture medium) using known processes and products available from commercial vendors. The purified proteins can then be "formulated", meaning buffer exchanged, sterilized, bulk-packaged, and/or packaged for a final user. Suitable formulations for pharmaceutical compositions include those described in Remington's Pharmaceutical Sciences, 18th ed. 1995, Mack Publishing Company, Easton, Pa.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropoietin, thrombopoeitin, calcitonin, IL-2, angiopoietin-2 (Maisonpierre et al. (1997), Science 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), Gene 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897,471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, Human Cytokines: Handbook for Basic and Clinical Research, all volumes (Aggarwal and Gutterman, eds. Blackwell Sciences, Cambridge, Mass., 1998); Growth Factors: A Practical Approach (McKay and Leigh, eds., Oxford University Press Inc., New York, 1993); and The Cytokine Handbook, Vols. 1 and 2 (Thompson and Lotze eds., Academic Press, San Diego, Calif., 2003).

Additionally, the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767, 0640, IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in Leukocyte Typing VI (Proceedings of the kWh International Workshop and Conference, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

Examples of antibodies that can be produced include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86

(B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEUF receptor, hepatocyte growth factor, osteoprotegerin ligand, interferon gamma, B lymphocyte stimulator (BlyS, also known as BAH', THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, integrins (including integrins comprising alpha4beta7), TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*.

Specific examples of known antibodies which can be produced using the methods of the invention include but are not limited to adalimumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, etrolizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262: 1401-05; Harbury et al. (1994), *Nature* 371:80-83; Hakansson et al. (1999), *Structure* 7:255-64. Specifically included among such recombinant fusion proteins are proteins in which a portion of a receptor is fused to an Fc portion of an antibody such as etanercept (a p75 INFR:Fc), abatacept and belatacept (CTLA4:Fc).

The invention is further described by reference to the following examples, which are intended to exemplify the claimed invention but not to limit it in any way.

EXAMPLES

Unless otherwise stated, all starting materials were obtained from commercial sources such as Sigma Aldrich, St. Louis, Mo., or were obtained using literature procedures.

$^1$H-NMR spectra were typically acquired on a Varian MR-400 spectrometer system (Varian, Palo Alto, Calif.) operating at a $^1$H frequency of 399.79 MHz, equipped with DUAL BB PFG and ATB probe 5 mm PFG probes with a z-axis gradient; or on a Bruker Avance II 400 spectrometer operating at a $^1$H frequency of 400.23 MHz, equipped with a Bruker 5 mm PABBO probe with a z-axis gradient. Samples were typically dissolved in 500 µL DMSO-$d_6$, CD$_3$OD, CDCl$_3$, or another deuterated NMR solvent for NMR analysis. $^1$H chemical shifts are referenced to the residual solvent signals from DMSO-$d_6$ at δ 2.50, CD$_3$OD at δ 3.30, or other reference solvents, or may be referenced to tetramethylsilane. Significant peaks were tabulated and typically include: number of protons, multiplicity (s, singlet; d, doublet; dd, doublet of doublets; t, triplet; q, quartet; m, multiplet; br s, broad singlet) and coupling constant(s) in Hertz.

Electron Ionization (EI) mass spectra were typically recorded on an Agilent Technologies 1100 LC/MSD SL Quadrupole LC/MS, Shimadzu LCMS-2020 Quadrupole, or Applied Biosystems API-2000 LC/MS/MS Triple Quadrupole mass spectrometer. Mass spectrometry results are reported as the ratio of mass over charge.

The following Abbreviations are used to refer to various reagents and solvents:

Ac Acetyl

Ac$_2$O Acetic anhydride

AcOH Acetic acid

Bn Benzyl

BnBr Benzyl bromide n-BuLi n-butyllithium

DCM Dichloromethane

DMF N,N-Dimethylformamide

DMSO Dimethylsulfoxide

EtOAc Ethyl Acetate

EtOH Ethanol

LiHMDS Lithium bis(trimethylsilyl)amide

Me Methyl

MeOH Methanol

POM Pivaloyloxymethyl

POM-Cl Pivaloyloxymethyl chloride iPr$_2$NEt N,N-Diisopropylethylamine

Py Pyridine

Pyr Pyridine rt Room Temperature

TBS t-Butyldimethylsilyl

TBSOTf t-Butyldimethylsilyl trifluoromethanesulfonate

TEA Triethylamine

TEAF Tetraethylammonium fluoride

TES Triethylsilane

TFA Trifluoroacetic acid

THF Tetrahydrofuran

TMSBr Bromotrimethylsilane

TMSCF$_3$ Trifluoromethyltrimethylsilane

19

Preparation of Examples

Example 1

(2S,3S,4R,5R,6S)-2-((bis((pivaloyloxy)methoxy)phosphoryl)methyl)-6-methyltetrahydro-2H-pyran-3,4,5-triyl triacetate

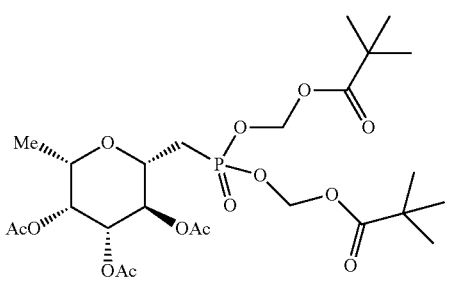 [SMILES: CC(=O)O[C@@H]1[C@H](OC(C)=O)[C@H](C)O[C@H](CP(=O)(OCOC(=O)C(C)(C)C)OCOC(=O)C(C)(C)C)[C@H]1OC(C)=O]

Example 1 was synthesized as shown in Scheme 1.

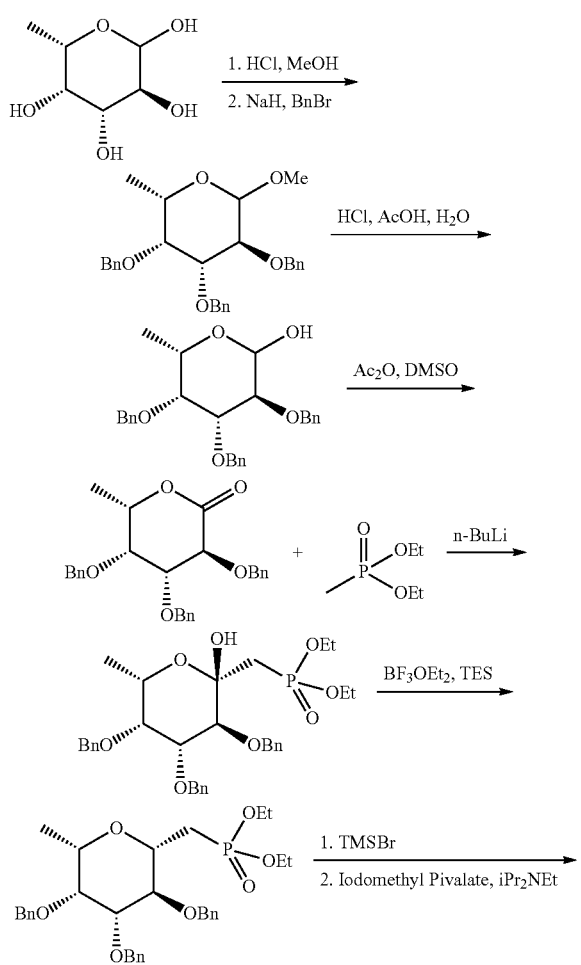

20

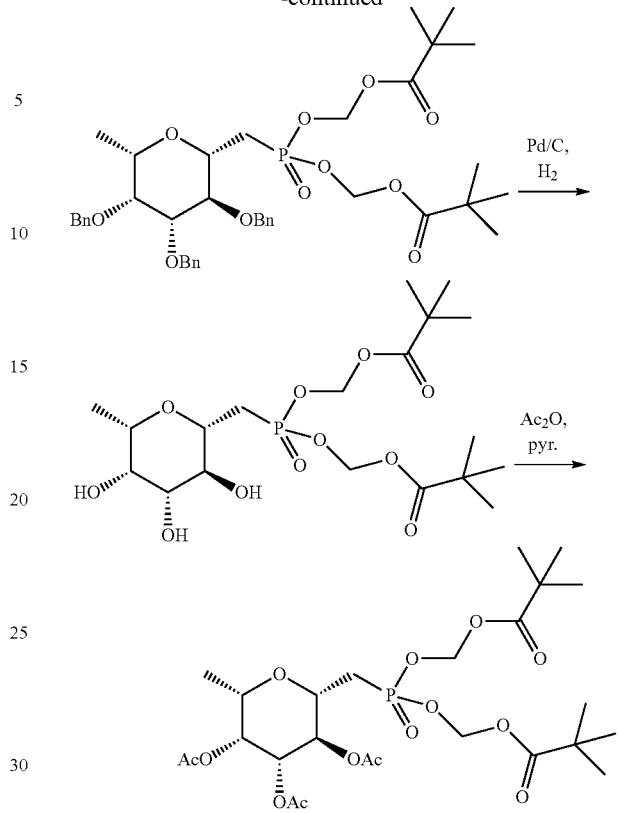

(2R,3S,4R,5R,6S)-3,4,5-tris(benzyloxy)-2-methoxy-6-methyltetrahydro-2H-pyran: Acetyl chloride (1.28 mL, 18 mmol, commercially available from Sigma Aldrich) was added dropwise to MeOH (40 mL) at 0° C., and the mixture was warmed to rt for 10 minutes before L-fucose (2.90 g, 17.7 mmol, TCI) was added. This mixture was then heated at reflux for 7 h and then cooled to rt. Anhydrous sodium carbonate (2.65 g, 25.0 mmol) was added, and then the mixture was stirred overnight at rt. The resulting suspension was filtered, and the filtrate was concentrated in vacuo to give (3S,4R,5S,6S)-2-methoxy-6-methyltetrahydro-2H-pyran-3,4,5-triol as a white solid mixture of 3 compounds (3.31 g, 105% yield). This material was used directly in the next step without characterization.

Sodium hydride (60% dispersion, 2.97 g, 74.3 mmol, commercially available from Sigma Aldrich) was added to a solution of the material obtained as described above (3.31 g, 18.6 mmol) in DMF (60 mL). The resulting mixture was stirred under argon for 30 min and then benzyl bromide (8.84 mL, 74.3 mmol, commercially available from Sigma Aldrich) was added dropwise. This mixture was stirred at rt for 3 h and then saturated aqueous ammonium chloride solution was added. The mixture was then partitioned between EtOAc and water, the layers were separated, and the organic layer was washed with water (2x), dried over anhydrous magnesium sulfate, filtered, and concentrated in vacuo to give an oil. This oil was purified by silica gel chromatography (15% EtOAc/hexane) to give (2R,3S,4R,5R,6S)-3,4,5-tris(benzyloxy)-2-methoxy-6-methyltetrahydro-2H-pyran as a colorless oil (3.17 g, 38.0% yield). $^1$H NMR (400 MHz, CDCl$_3$): δ ppm 1.11 (d, J=6.46 Hz, 3 H) 3.35 (s, 3 H) 3.63 (d, J=1.96 Hz, 1 H) 3.83 (q, J=6.46 Hz, 1 H) 3.92 (dd, J=9.98, 2.74 Hz, 1 H) 4.03 (dd, J=10.17, 3.72 Hz, 1 H) 4.63-4.67 (m, 2 H) 4.69 (d, J=12.13

Hz, 1 H) 4.73 (d, J=11.93 Hz, 1 H) 4.83 (dd, J=12.13, 1.00 Hz, 1 H) 4.88 (d, J=11.93 Hz, 1 H) 4.98 (d, J=11.54 Hz, 1 H) 7.14-7.47 (m, 15 H).

(3S,4R,5R,6S)-3,4,5-tris(benzyloxy)-6-methyltetrahydro-2H-pyran-2-ol: A solution of 80% acetic acid in water (45 mL), aqueous HCl (1N, 12.5 mL), and (2R,3S,4R,5R,6S)-3,4,5-tris(benzyloxy)-2-methoxy-6-methyltetrahydro-2H-pyran (3.10 g, 6.91 mmol) was heated at reflux for 4 h and then cooled to rt. The product was extracted into DCM (2×), and the combined extracts were washed with saturated aqueous sodium bicarbonate solution (2×), dried over anhydrous magnesium sulfate, filtered, and concentrated in vacuo to give an oil. The oil was purified by silica gel chromatography (20 to 100% EtOAc/hexanes gradient) to give (3S,4R,5R,6S)-3,4,5-tris(benzyloxy)-6-methyltetrahydro-2H-pyran-2-ol as a colorless oil (2.22 g, 73.9% yield, 1:1 mixture of anomers). ESI (M+Na) 457.1; calc for $C_{27}H_{30}O_5$ 434.2.

(3S,4R,5R,6S)-3,4,5-tris(benzyloxy)-6-methyltetrahydro-2H-pyran-2-one: Acetic anhydride (7.40 mL, 78 mmol, commercially available from Sigma Aldrich) was added to a solution of (3S,4R,5R,6S)-3,4,5-tris(benzyloxy)-6-methyltetrahydro-2H-pyran-2-ol (1.70 g, 3.91 mmol) in DMSO (12 mL), and the resulting mixture was stirred for 24 h at P. EtOAc was added, and the mixture was washed with water (3×), dried over anhydrous magnesium sulfate, filtered, and concentrated in vacuo to give an oil. The oil was purified by silica gel chromatography (0 to 40% EtOAc/hexanes gradient) to give (3S,4R,5R,6S)-3,4,5-tris(benzyloxy)-6-methyltetrahydro-2H-pyran-2-one as a colorless oil (1.06 g, 62.6% yield). ESI (M+H) 433.1; calc for $C_{27}H_{28}O_5$ 432.2.

Diethyl (((2S,3S,4R,5R,6S)-3,4,5-tris(benzyloxy)-2-hydroxy-6-methyltetrahydro-2H-pyran-2-yl)methyl)phosphonate: n-Butyllithium (2.5 M in hexanes, 0.64 mL, 1.59 mmol, commercially available from Sigma Aldrich) was added to a stirred solution of diethyl methylphosphonate (0.23 mL, 1.59 mmol, commercially available from Sigma Aldrich) in THF (1.5 mL) at −78° C. under an argon atmosphere. The mixture was stirred for 15 min before a solution of (3 S,4R,5R,6S)-3,4,5-tris(benzyloxy)-6-methyltetrahydro-2H-pyran-2-one (0.275 g, 0.636 mmol) in THF (1 mL) at −78° C. was added. The reaction mixture was removed from the cooling bath, and the mixture was allowed to warm to room temperature while stirring for 1 h. The reaction mixture was next concentrated in vacuo. The resulting oil was purified by silica gel chromatography (0 to 75% EtOAc/hexanes gradient) to give diethyl (((2S,3S,4R,5R,6S)-3,4,5-tris(benzyloxy)-2-hydroxy-6-methyltetrahydro-2H-pyran-2-yl)methyl)phosphonate as a colorless oil (0.251 g, 67.5% yield). $^1$H NMR (400 MHz, CDCl$_3$): δ ppm 1.09 (d, J=6.65 Hz, 3 H) 1.26 (q, J=6.85 Hz, 6 H) 1.76 (dd, J=18.49, 15.16 Hz, 1 H) 2.33 (dd, J=17.41, 15.26 Hz, 1 H) 3.68 (br. d, J=1.60 Hz, 1 H) 3.72 (d, J=9.98 Hz, 1 H) 3.92-4.02 (m, 2 H) 4.06-4.17 (m, 4 H) 4.69 (dd, J=11.54, 4.11 Hz, 2H) 4.77 (dd, J=16.43, 11.74 Hz, 2 H) 4.99 (dd, J=11.54, 9.39 Hz, 2 H) 7.26-7.41 (m, 15 H).

Diethyl (((2S,3S,4R,5R,6S)-3,4,5-tris(benzyloxy)-6-methyltetrahydro-2H-pyran-2-yl)methyl)phosphonate: Boron trifluoride diethyl etherate (0.079 mL, 0.644 mmol, commercially available from Sigma Aldrich) and triethylsilane (0.103 mL, 0.644 mmol, Sigma Aldrich) were added to a stirred solution of diethyl (((2S,3S,4R,5R,6S)-3,4,5-tris(benzyloxy)-2-hydroxy-6-methyltetrahydro-2H-pyran-2-yl)methyl)phosphonate (0.251 g, 0.429 mmol) in acetonitrile (2 mL) at 0° C. under an argon atmosphere. The reaction mixture was then stirred at 0° C. for 5 h. The reaction mixture was next partitioned between EtOAc and saturated aqueous sodium bicarbonate. The organic layer was separated, dried over anhydrous magnesium sulfate, filtered, and concentrated in vacuo. The resulting oil was purified by silica gel chromatography (30 to 100% EtOAc/hexanes gradient) to give diethyl (((2S,3S,4R,5R,6S)-3,4,5-tris(benzyloxy)-6-methyltetrahydro-2H-pyran-2-yl)methyl)phosphonate as a colorless oil (0.220 g, 90% yield). $^1$H NMR (400 MHz, CDCl$_3$): δ ppm 1.14 (d, J=6.26 Hz, 3 H) 1.26 (td, J=7.04, 1.96 Hz, 6 H) 1.92 (td, J=15.75, 9.78 Hz, 1 H) 2.29 (ddd, J=19.95, 15.36, 1.47 Hz, 1 H) 3.53 (q, J=6.39 Hz, 1H) 3.56-3.70 (m, 4 H) 3.98-4.11 (m, 4 H) 4.63-4.77 (m, 4 H) 4.97 (dd, J=11.44, 1.86 Hz, 2 H) 7.26-7.39 (m, 15 H).

(((((2S,3S,4R,5R,6S)-3,4,5-tris(benzyloxy)-6-methyltetrahydro-2H-pyran-2-yl)methyl)phosphoryl)bis(oxy))bis(methylene)bis(2,2-dimethylpropanoate): Bromotrimethylsilane (0.255 mL, 1.93 mmol, commercially available from Sigma Aldrich) was added dropwise to a stirred solution of diethyl (((2S,3S,4R,5R,6S)-3,4,5-tris(benzyloxy)-6-methyltetrahydro-2H-pyran-2-yl)methyl)phosphonate (0.110 g, 0.193 mmol) in DCM (6 mL) at 0° C. The cooling bath was removed, and the reaction mixture was allowed to warm to room temperature and stir for 21 h. The reaction mixture was concentrated in vacuo. The resulting residue was dissolved in MeOH and stirred for 2 h. The solution was then concentrated in vacuo to give (((2S,3S,4R,5R,6S)-3,4,5-tris(benzyloxy)-6-methyltetrahydro-2H-pyran-2-yl)methyl)phosphonic acid as a light orange oil (0.103 g, 104% yield). The material thus obtained was taken on without further purification.

N,N-Diisopropylethylamine (0.168 mL, 0.966 mmol) and iodomethyl pivalate (0.468 g, 1.93 mmol) were added to a stirred solution of (((2S,3S,4R,5R,6S)-3,4,5-tris(benzyloxy)-6-methyltetrahydro-2H-pyran-2-yl)methyl)phosphonic acid (0.099 g, 0.193 mmol) in acetonitrile (5 mL). The reaction mixture was stirred at room temperature for 20 h. The reaction mixture was then concentrated in vacuo. The resulting oil was purified by silica gel chromatography (0 to 50% EtOAc/hexanes gradient) to give (((((2S,3S,4R,5R,6S)-3,4,5-tris(benzyloxy)-6-methyltetrahydro-2H-pyran-2-yl)methyl)phosphoryl)bis(oxy))bis(methylene)bis(2,2-dimethylpropanoate) as a colorless oil that partially solidified upon standing (0.058 g, 40.5% yield). $^1$H NMR (400 MHz, CDCl$_3$) δ ppm 1.16 (d, J=6.26 Hz, 3 H) 1.19 (s, 9 H) 1.20 (s, 9 H) 2.05 (ddd, J=17.02, 15.55, 9.88 Hz, 1 H) 2.41 (ddd, J=19.95, 15.36, 2.45 Hz, 1 H) 3.53 (q, J=6.52 Hz, 1 H) 3.56-3.74 (m, 4 H) 4.62-4.77 (m, 4 H) 4.97 (dd, J=11.35, 2.93 Hz, 2 H) 5.57-5.66 (m, 4 H) 7.26-7.38 (m, 15 H).

(((((2S,3S,4R,5S,6S)-3,4,5-trihydroxy-6-methyltetrahydro-2H-pyran-2-yl)methyl)phosphoryl)bis(oxy))bis(methylene)bis(2,2-dimethylpropanoate): Palladium (10 wt. % on activated carbon, 0.008 g, 0.008 mmol, commercially available from Sigma Aldrich) was added to a stirred solution of (((((2S,3S,4R,5R,6S)-3,4,5-tris(benzyloxy)-6-methyltetrahydro-2H-pyran-2-yl)methyl)phosphoryl)bis(oxy))bis(methylene)bis(2,2-dimethylpropanoate) (0.058 g, 0.078 mmol) in EtOH (1 mL) under an argon atmosphere. The reaction mixture was placed under a hydrogen atmosphere (balloon) and stirred at room temperature for 1 h. The reaction mixture was then filtered, and the filtrate was concentrated in vacuo to give (((((2S,3S,4R,5S,6S)-3,4,5-trihydroxy-6-methyltetrahydro-2H-pyran-2-yl)methyl)phosphoryl)bis(oxy))bis(methylene)bis(2,2-dimethylpropanoate) as a colorless oil (0.038 g, 103% yield). $^1$H NMR (400 MHz, CDCl$_3$) δ ppm 1.23 (s, 18 H) 1.30 (d, J=6.46 Hz, 3 H) 2.27-2.48 (m, 2 H) 3.50-3.61 (m, 2 H) 3.64 (q, J=6.46 Hz, 1H) 3.71-3.78 (m, 2 H) 5.61-5.70 (m, 4 H).

(2S,3S,4R,5R,6S)-2-((bis((pivaloyloxy)methoxy)phosphoryl)methyl)-6-methyltetrahydro-2H-pyran-3,4,5-triyl triacetate: Acetic anhydride (0.046 mL, 0.485 mmol, commercially available from Sigma Aldrich) was added dropwise to a stirred mixture of (((((2S,3S,4R,5S,6S)-3,4,5-trihydroxy-6-methyltetrahydro-2H-pyran-2-yl)methyl)phosphoryl)bis(oxy))bis(methylene)bis(2,2-dimethylpropanoate) (0.038 g, 0.081 mmol) and 4-dimethylaminopyridine (0.0005 g, 0.004 mmol) in pyridine (0.5 mL) at 0° C. under an argon atmosphere. The cooling bath was removed, and the reaction mixture was allowed to warm to room temperature and stir for 2 h. The reaction mixture was then diluted with DCM. The organic mixture was washed with saturated aqueous potassium bisulfate (3×) and with saturated aqueous sodium chloride. The organic layer was then dried over anhydrous magnesium sulfate, filtered, and concentrated in vacuo to give (2S,3S,4R,5R,6S)-2-((bis((pivaloyloxy)methoxy)-phosphoryl)methyl)-6-methyltetrahydro-2H-pyran-3,4,5-triyl triacetate as a colorless oil (0.045 g, 93% yield). ESI (M+Na) 619.1; calc for $C_{25}H_{41}O_{14}P$ 596.2; $^1H$ NMR (400 MHz, $CD_3OD$) δ ppm 1.19 (d, J=6.26 Hz, 3 H) 1.26 (s, 9H) 1.27 (s, 9 H) 1.96 (s, 3 H) 2.08 (s, 3 H) 2.13-2.20 (m, 1 H) 2.18 (s, 3 H) 2.29 (ddd, J=20.74, 15.65, 2.93 Hz, 1 H) 3.88 (ddd, J=20.15, 9.59, 2.90 Hz, 1 H) 3.96 (qd, J=6.33, 0.60 Hz, 1 H) 5.05 (t, J=9.60 Hz, 1 H) 5.12 (dd, J=9.98, 3.33 Hz, 1 H) 5.29 (dd, J=3.23, 0.68 Hz, 1 H) 5.63-5.74 (m, 4 H).

Example 2

(2S,3S,4R,5R,6S)-2-((bis(acetoxymethoxy)phosphoryl)methyl)-6-methyltetrahydro-2H-pyran-3,4,5-triyl triacetate

2

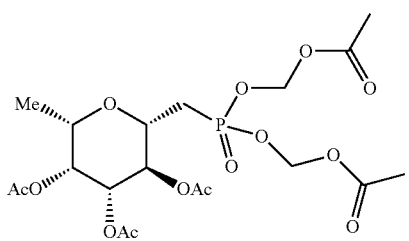

This compound was synthesized by the same procedure used for the synthesis of (2S,3S,4R,5R,6S)-2-((bis((pivaloyloxy)methoxy)phosphoryl)methyl)-6-methyltetrahydro-2H-pyran-3,4,5-triyl triacetate, but using bromomethyl acetate (commercially available from Sigma Aldrich) instead of iodomethyl pivalate: ESI (M+H) 513.0; calc for $C_{19}H_{29}O_{14}P$ 512.4; $^1H$ NMR (400 MHz, $CD_3OD$) δ ppm 5.71-5.61 (m, 4 H) 5.29 (dd, J=3.33, 0.78 Hz, 1 H) 5.12 (dd, J=3.33, 10.17 Hz, 1 H) 5.05 (dd, J=9.59, 9.98 Hz, 1 H) 4.00-3.83 (m, 2 H) 2.35-2.17 (m, 2 H) 2.18 (s, 3 H) 2.16 (s, 3 H) 2.15 (s, 3 H) 2.09 (s, 3 H) 1.96 (2, 3 H) 1.18 (d, J=6.46 Hz, 3 H).

Example 3

(2R,3S,4R,5S,6R)-2-((bis((pivaloyloxy)-methoxy)phosphoryl)methyl)-6-(trifluoromethyl)tetrahydro-2H-pyran-3,4,5-triyl triacetate

3

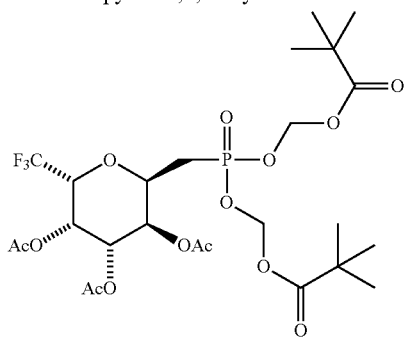

Example 3 was synthesized as shown in Scheme 2.

Scheme 2

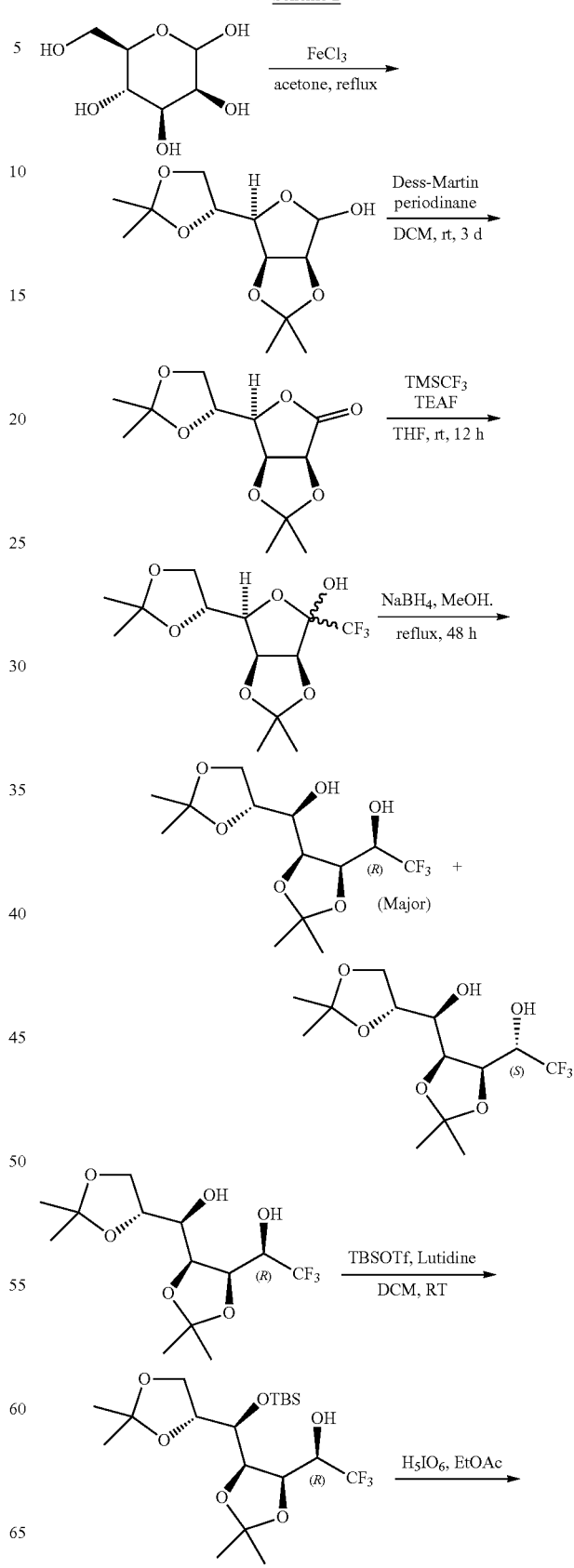

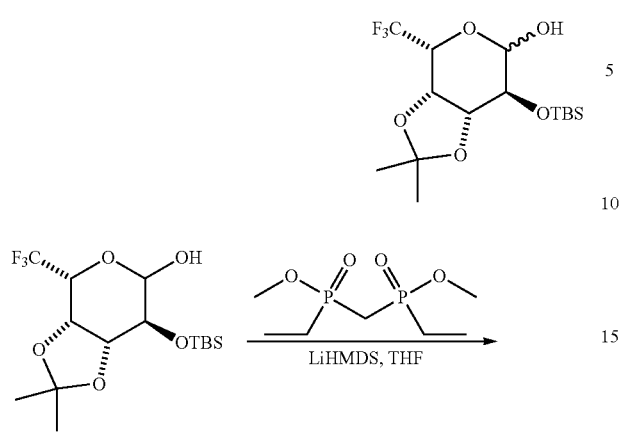

(Minor)

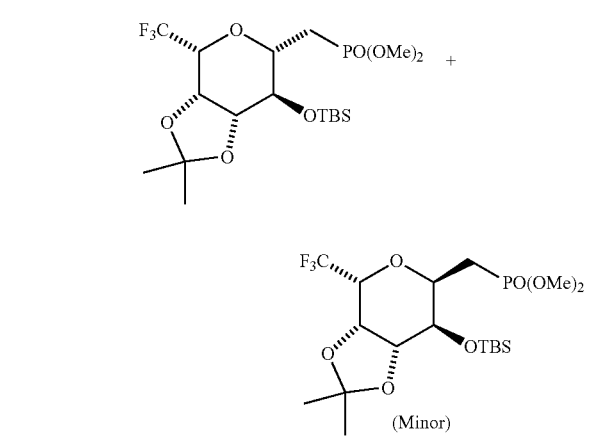

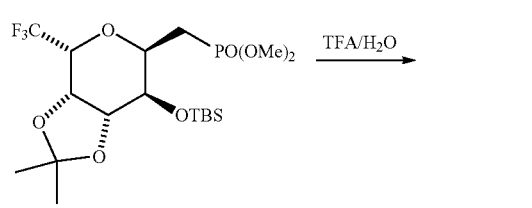

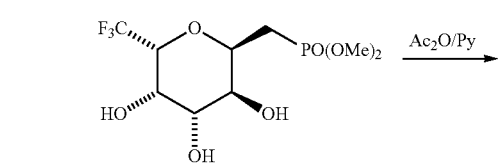

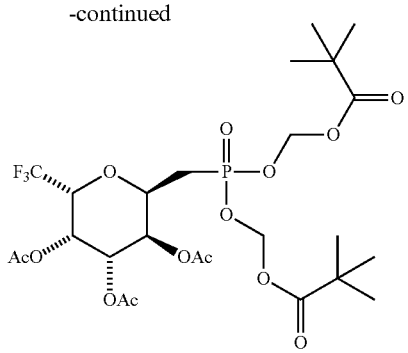

(3aS,6R,6aS)-6-((R)-2,2-dimethyl-1,3-dioxolan-4-yl)-2,2-dimethyltetrahydrofuro[3,4-d][1,3]dioxol-4-ol: In a 1000 mL three neck round bottom flask, ferric chloride (4.4 g, 27.0 mmol, Rankem, India) was added to a solution of D-(+) mannose (100 g, 555 mmol, commercially available from Sigma Aldrich, India) in acetone (1400 mL) at rt under a nitrogen atmosphere. The reaction mixture was stirred at 85° C. for 3 h. Upon completion of the reaction (TLC, 30% EtOAc-hexanes $R_f$ 0.5), the reaction mixture was cooled in an ice-bath and neutralized with 10% $K_2CO_3$ solution (1000 mL, Rankem, India). The volatiles were distilled off under reduced pressure, and the aqueous residue obtained was extracted with EtOAc (1000 mL×2). The combined organic extracts were washed with water (500 mL), brine (500 mL), dried over anhydrous $Na_2SO_4$ and concentrated under reduced pressure. The residue obtained was washed successively with n-pentane to give (3aS,6R,6aS)-6-((R)-2,2-dimethyl-1,3-dioxolan-4-yl)-2,2-dimethyltetrahydrofuro[3,4-d][1,3]dioxol-4-ol as a colorless solid (96 g, 66% yield): $^1$H NMR (400 MHz, CDCl$_3$) δ 5.37 (s, 1H), 4.79 (dd, J=3.6, 5.6 Hz, 1H), 4.60 (d, J=6.0 Hz, 1H), 4.41-4.38 (m, 1H), 4.16 (dd, J=4.0, 7.2 Hz, 1H), 4.09-4.03 (m, 2H), 3.06 (br s, 1H), 1.46 (s, 3H), 1.45 (s, 3H), 1.37 (s, 3H), 1.32 (s, 3H).

(3aS,6R,6aS)-6-((R)-2,2-dimethyl-1,3-dioxolan-4-yl)-2,2-dimethyldihydrofuro[3,4-d][1,3]dioxol-4(3aH)-one: In a 1000 mL round bottom flask, Dess-Martin periodinane (110 g, 261.62 mmol, Spectrochem, India) was added to a solution of (3aS,6R,6aS)-6-((R)-2,2-dimethyl-1,3-dioxolan-4-yl)-2,2-dimethyltetrahydrofuro[3,4-d][1,3]dioxol-4-ol (45 g, 174 mmol) in anhydrous DCM (900 mL) at rt. The resulting mixture was stirred for 15 minutes and treated with t-BuOH (14.16 g, 191.4 mmol, Rankem, India) at rt. The resulting reaction mixture was stirred at rt for 3 days under an argon atmosphere. Upon completion of the reaction (TLC, 30% EtOAc-hexanes, $R_f$ 0.55), the reaction mixture was quenched with aqueous $Na_2S_2O_3$ (1000 mL) and extracted with DCM (4×250 mL). The combined organic extracts were washed with saturated NaHCO$_3$ (500 mL), brine (200 mL), and then dried over anhydrous Na$_2$SO$_4$. The solution was concentrated under reduced pressure, and the residue obtained was washed with n-pentane to give (3aS,6R,6aS)-6-((R)-2,2-dimethyl-1,3-dioxolan-4-yl)-2,2-dimethyldihydrofuro[3,4-d][1,3]dioxol-4(3aH)-one as a colorless solid (35 g, 78%): $^1$H NMR (400 MHz, CDCl$_3$) δ 4.87 (dd, J=3.2, 5.2 Hz, 1H), 4.83 (d, J=5.2 Hz, 1H), 4.43-4.31 (m, 1H), 4.38-4.37 (m, 1H), 4.13 (dd, J=5.7, 9.2 Hz, 1H), 4.06 (dd, J=5.6, 9.2 Hz, 1H), 1.48 (s, 3H), 1.46 (s, 3H), 1.42 (s, 3H), 1.39 (s, 3H).

(3aS,6R,6aS)-6-((R)-2,2-dimethyl-1,3-dioxolan-4-yl)-2,2-dimethyl-4-(trifluoromethyl)tetrahydrofuro[3,4-d][1,3]-dioxol-4-ol: In a 1000 mL three neck round bottom flask, a solution of (3aS,6R,6aS)-6-((R)-2, 2-dimethyl-1, 3-dioxolan-4-yl)-2, 2-dimethyldihydrofuro[3,4-d][1,3]dioxol-4(3aH)-one (30 g, 116.2 mmol, 1eq) in THF (600 mL) was treated with TMSCF$_3$ (2M in THF, 122 mL, 244 mmol, commercially available from Sigma Aldrich, India) and tetraethylammonium fluoride (TEAF, 2.48 g, 23.24 mmol, Apollo scientific, UK) at rt under a nitrogen atmosphere. The reaction mixture was stirred at rt for 30 minutes and additional TEAF (24.8 g, 232.4 mmol, Apollo scientific, UK) was added to the reaction mixture. The resulting reaction mixture was stirred at rt for 12 h under a nitrogen atmosphere. Upon completion of the reaction (TLC, 30% EtOAc-hexanes, $R_f$ 0.6), the reaction mixture was diluted with water (1000 mL), and it was then extracted with EtOAc (500 mL×2). The combined organic extracts were washed with water (250 mL), brine (250 mL) and dried over anhydrous $Na_2SO_4$. The solution was concentrated under reduced pressure. The residue obtained was purified by silica gel (60-120 mesh) column chromatography (gradient elution, 5-10% EtOAc-hexanes) to give (3aS,6R,6aS)-6-((R)-2,2-dimethyl-1,3-dioxolan-4-yl)-2,2-dimethyl-4-(trifluoromethyl)tetrahydrofuro[3,4-d][1,3]-dioxol-4-ol, as a yellow semi solid mixture of two isomers (27.3 g, 71.8%): $^1$H NMR (400 MHz, $CDCl_3$) δ 4.95 (m, 2H), 4.78 (d, J=8 Hz, 1H), 4.61-4.32 (m, 2H), 4.23 (dd, J=8, 4 Hz, 1H), 4.18-4.10 (m, 3H), 4.06 (dd, J=8.0, 4.0 Hz, 2H), 3.98 (m, 1H), 1.52 (s, 3H), 1.47 (s, 3H), 1.46 (s, 3H), 1.40 (s, 3H), 1.39 (s, 3H), 1.36 (s, 3H); $^{19}$F NMR (376.17 MHz, $CDCl_3$) δ −78.24 & −82.32 ppm.

(R)-1-((4R,5S)-5-((R)—((R)-2,2-dimethyl-1,3-dioxolan-4-yl) (hydroxy)methyl)-2,2-dimethyl-1,3-dioxolan-4-yl)-2,2,2-trifluoroethanol, and (S)-1-((4R,5S)-5-((R)—((R)-2,2-dimethyl-1,3-dioxolan-4-yl)(hydroxy)methyl)-2,2-dimethyl-1,3-dioxolan-4-yl)-2,2,2-trifluoroethanol: In a 1000 mL three neck round bottom flask, a solution of (3aS, 6R,6aS)-6-((R)-2,2-dimethyl-1,3-dioxolan-4-yl)-2,2-dimethyl-4-(trifluoromethyl)tetrahydrofuro[3,4-d][1,3]-dioxol-4-ol (25 g, 76.21 mmol) in MeOH (500 mL) was treated with $NaBH_4$ (57 g, 1.52 mol, commercially available from Sigma Aldrich, India) in portions at rt. During addition of the $NaBH_4$, excessive frothing was observed, hence slow addition is recommended. The resulting reaction mixture was refluxed (after internal temperature returned to rt) for 25 h. Upon completion of reaction (TLC, 30% EtOAc-hexanes, $R_f$ 0.4), the reaction mixture was concentrated under reduced pressure to remove the solvent. The residue obtained was diluted with water (1000 mL) and extracted with EtOAc (2×500 mL). The combined organic extract was washed with water (250 mL), brine (250 mL) and dried over anhydrous $Na_2SO_4$. The solution was concentrated under reduced pressure and the residue obtained was purified by silica gel (60-120 mesh) column chromatography (gradient elution, 10-15% EtOAc-hexanes) to give (R)-1-((4R,5S)-5-((R)—((R)-2,2-dimethyl-1,3-dioxolan-4-yl)(hydroxy)methyl)-2,2-dimethyl-1,3-dioxolan-4-yl)-2,2,2-trifluoroethanol as the major product and (S)-1-((4R,5S)-5-((R)—((R)-2,2-dimethyl-1,3-dioxolan-4-yl)(hydroxy)methyl)-2,2-dimethyl-1,3-dioxolan-4-yl)-2,2,2-trifluoro ethanol as the minor product. (R)-1-((4R,5S)-5-((R)—((R)-2,2-dimethyl-1,3-dioxolan-4-yl)(hydroxy)methyl)-2,2-dimethyl-1,3-dioxolan-4-yl)-2,2,2-trifluoroethanol (13.0 g, 51%): $^1$H NMR (400 MHz, $CDCl_3$) δ 4.47 (s, 1H), δ 4.24 (m, 1H), 4.18-4.11 (m, 1H), 4.11-3.99 (m, 2H), 3.76 (d, J=8 Hz, 1H), 3.68 (t, J=8, 12 Hz, 1H), 2.86 (d, J=4.0 Hz, 1H), 1.58 (s, 3H), 1.42 (s, 3H), 1.41 (s, 3H), 1.36 (s, 3H); $^{19}$F NMR (376.17 MHz, $CDCl_3$) δ −76.30 ppm. (S)-1-((4R,5S)-5-((R)—((R)-2,2-dimethyl-1,3-dioxolan-4-yl)(hydroxy)methyl)-2,2-dimethyl-1,3-dioxolan-4-yl)-2,2,2-trifluoroethanol: $^1$H NMR (400 MHz, $CDCl_3$) δ 4.46 (d, J=8.0 Hz, 1H), 4.45-438 (m, 1H), 4.33 (t, J=8, 12 Hz, 1H), 4.13-405 (m, 4H), 3.96 (t, J=8, 16 Hz, 1H), 2.58 (d, J=8.0 Hz, 1H), 1.50 (s, 3H), 1.41 (s, 3H), 1.40 (s, 3H), 1.36 (s, 3H); $^{19}$F NMR (376.17 MHz, $CDCl_3$) δ −75.03 ppm.

(R)-1-((4R,5R)-5-((R)-((tert-butyldimethylsilyl)oxy) ((R)-2,2-dimethyl-1,3-dioxolan-4-yl)methyl)-2,2-dimethyl-1,3-dioxolan-4-yl)-2,2,2-trifluoroethanol: In a 100 mL 2 neck round bottom flask, (R)-1-((4R,5S)-5-((R)—((R)-2,2-dimethyl-1,3-dioxolan-4-yl)(hydroxy)methyl)-2,2-dimethyl-1,3-dioxolan-4-yl)-2,2,2-trifluoroethanol (1 g, 3.03 mmol) and 2,6-lutidine (1 g, 9.09 mmol, commercially available from Sigma Aldrich, India) was taken up in dry DCM (50 mL) at 0° C. under a nitrogen atmosphere. TBSOTf (2.4 g, 9.09 mmol, commercially available from Sigma Aldrich, India) was added to the above reaction mixture at the same temperature under a nitrogen atmosphere. The reaction mixture was stirred for 30 min at 0° C. and then the temperature was slowly raised to rt and the mixture stirred at rt for 3 h. Upon completion of the reaction (TLC, 20% EtOAc in hexane $R_f$ 0.5), the reaction mixture was quenched with saturated $NaHCO_3$ solution and extracted with EtOAc (3×20 mL). The combined organic extracts were washed with water (20 mL) and brine (20 mL), and were then concentrated under reduced pressure. The residue obtained was purified by silica gel (60-120 mesh) column chromatography (gradient elution 10-15% EtOAc-hexanes) to give (R)-1-((4R,5R)-5-((R)-((tert-butyldimethylsilyl)oxy)((R)-2,2-dimethyl-1,3-dioxolan-4-yl)methyl)-2,2-dimethyl-1,3-dioxolan-4-yl)-2,2,2-trifluoroethanol as a pale yellow oil (0.7 g, 50%): $^1$H NMR (400 MHz, $CDCl_3$) δ 4.52-4.45 (m, 2H), 4.29-4.25 (m, 1H), 4.22-4.19 (m, 1H), 4.04-3.93 (m, 2H), 3.78-3.74 (t, J=8.0 Hz, 1H), 2.70 (d, J=11.2 Hz, 1H), 1.55 (s, 3H), 1.40 (d, J=9.6 Hz, 3H), 0.86 (s, 9H), 0.11 (d, J=3.2 Hz, 6H), 5 H were obscured.

(3aS,4R,7S,7aR)-7-((tert-butyldimethylsilyl)oxy)-2,2-dimethyl-4-(trifluoromethyl)tetrahydro-3aH-[1,3]dioxolo[4,5-c]pyran-6-ol: In a 50 mL round bottom flask, a stirred solution of (R)-1-((4R,5R)-5-((R)-((tert-butyldimethylsilyl)oxy)((R)-2,2-dimethyl-1,3-dioxolan-4-yl)methyl)-2,2-dimethyl-1,3-dioxolan-4-yl)-2,2,2-trifluoroethanol (0.5 g, 1.12 mmol) in EtOH (10 mL) was treated with $H_5IO_6$ (0.25 g, 1.12 mmol, Spectrochem, India) at 0° C. The reaction mixture was stirred at rt for 2 h. Upon completion of the reaction (TLC, 10% EtOAc in hexane $R_f$ 0.4), the reaction mixture was diluted with saturated $NaHCO_3$ solution (5 mL), water (10 mL) and extracted with EtOAc (2×20 mL). The combined organic extracts were washed with brine solution (20 mL) and concentrated under reduced pressure. The residue obtained was purified by silica gel (60-120 mesh) column chromatography (elution 15% EtOAc-hexanes) to give (3aS,4R,7S,7aR)-7-((tert-butyldimethylsilyl)oxy)-2,2-dimethyl-4-(trifluoromethyl)tetrahydro-3aH-[1,3]dioxolo[4,5-c]pyran-6-ol as a sticky oil (4:1 mixture of anomers, 0.2 g, 48.7%): $^1$H NMR (400 MHz, $CDCl_3$) δ 5.25-5.22 (m, 1H), 4.49-4.37 (m, 2H), 4.01-3.99 (m, 1H), 3.49-3.47 (d, J=9.2 Hz, 1H), 1.55 (s, 3H), 1.37 (s, 3H), 0.93 (s, 9H), 0.17 (d, 6H); $^{19}$F NMR (376.17 MHz, $CDCl_3$) δ −72.73 ppm.

Dimethyl (((3aS,4R,6S,7S,7aR)-7-((tert-butyldimethylsilyl)oxy)-2,2-dimethyl-4-(trifluoromethyl)tetrahydro-3aH-[1,3]dioxolo[4,5-c]pyran-6-yl) methyl)phosphonate and dimethyl (((3aS,4R,6R,7S,7aR)-7-((tert-butyldimethylsilyl)oxy)-2,2-dimethyl-4-(trifluoromethyl)tetrahydro-3aH-[1,3]dioxolo[4,5-c]pyran-6-yl)methyl)phosphonate: In a 25 mL round bottom flask, a stirred solution of (3aS,4R,7S,7aR)-7-((tert-butyldimethylsilyl)oxy)-2,2-dimethyl-4-(trifluoromethyl)tetrahydro-3aH-[1,3]dioxolo[4,5-c]pyran-6-ol (400 mg, 1.07 mmol, 1eq), in dry THF (10 mL) maintained at 0° C. under nitrogen atmosphere, was treated with LiHMDS (1M in THF, 0.39 mL, 3.22 mmol, commercially available from Sigma Aldrich, India) at 0° C. The reaction mixture was stirred at 0° C. for 30 min under a nitrogen atmosphere and treated with tetramethyl methylenebis(phosphonate) (800 mg, 3.22 mmol, Alfa Asear, India) in THF (8 mL) at the same temperature. The resulting reaction mixture was stirred at rt for 36 h. Upon completion of the reaction (TLC, 30% EtOAc in hexane, $R_f$ 0.4), the reaction mixture was quenched with saturated $NaHCO_3$ solution at 0° C. and stirred for 5 min. The mixture was diluted with water (40 mL) and extracted with EtOAc (2×20 mL). The organic extract was washed with water, brine (20 mL), dried over anhydrous Na$_2$SO$_4$ and concentrated under reduced pressure. The residue obtained was purified by silica gel (60-120 mesh) column chromatography (gradient elution 5-10% EtOAc-hexanes) to give dimethyl (((3aS,4R,6S,7S,7aR)-7-((tert-butyldimethylsilyl)oxy)-2,2-dimethyl-4-(trifluoromethyl)tetrahydro-3aH-[1,3]dioxolo[4,5-c]pyran-6-yl)methyl)phosphonate and dimethyl (((3aS,4R,6R,7S,7aR)-7-((tert-butyldimethylsilyl)oxy)-2,2-dimethyl-4-(trifluoromethyl)tetrahydro-3aH-[1,3]dioxolo[4,5-c]pyran-6-yl)methyl)phosphonate as a sticky oils. Dimethyl (((3aS,4R,6S,7S,7aR)-7-((tert-butyldimethylsilyl)oxy)-2,2-dimethyl-4-(trifluoromethyl)tetrahydro-3aH-[1,3]dioxolo[4,5-c]pyran-6-yl)methyl)phosphonate (100 mg, 20%): $^1$H NMR (400 MHz, CDCl$_3$) δ 4.34-4.32 (m, 1H), 4.22-4.17 (m, 1H), 4.06 (t, J=6.0 Hz 1H), 3.74-3.69 (m, 7H), 3.60 (t, J=7.2 Hz 1H), 2.38-2.29 (m, 1H), 2.06-1.95 (m, 1H), 1.52 (s, 3H), 1.35 (s, 3H), 0.9 (s, 9H), 0.13 (s, 3H), 0.06 (s, 3H); $^{19}$F NMR (376.17 MHz, CDCl$_3$) δ −72.32 ppm. Dimethyl (((3aS,4R,6R,7S,7aR)-7-((tert-butyldimethylsilyl)oxy)-2,2-dimethyl-4-(trifluoromethyl)tetrahydro-3aH-[1,3]dioxolo[4,5-c]pyran-6-yl)methyl)phosphonate (70 mg, 14%): $^1$H NMR (400 MHz, CDCl$_3$) δ 4.50-4.42 (m, 1H), 4.39-4.32 (m, 1H), 4.22-4.18 (m, 1H), 4.11-4.04 (m, 1H), 3.82 (m, 1H), 3.76-3.70 (m, 6H), 2.14-1.87 (m, 2H), 1.52 (s, 3H), 1.35 (s, 3H), 0.9 (s, 9H), 0.13 (s, 3H), 0.06 (s, 3H) ppm.

Dimethyl (((2R,3S,4R,5S,6R)-3,4,5-trihydroxy-6-(trifluoro methyl)tetrahydro-2H-pyran-2-yl)methyl)phosphonate: In a 25 mL round bottom flask, dimethyl (((3aS,4R,6R,7S,7aR)-7-((tert-butyldimethylsilyl)oxy)-2,2-dimethyl-4-(trifluoromethyl)tetrahydro-3aH-[1,3]dioxolo[4,5-c]pyran-6-yl)methyl)phosphonate (70 mg, 0.14 mmol) was taken up in a TFA-H$_2$O mixture (2 mL, 9:1) at 0° C. The reaction mixture was gradually warmed to rt and stirred at rt for 3 h. Upon completion of the reaction (TLC, 50% EtOAc in hexanes, R$_f$ 0.1), the reaction mixture was concentrated under reduced pressure. The residue obtained was washed with n-pentane (10 mL) to give dimethyl (((2R,3S,4R,5S,6R)-3,4,5-trihydroxy-6-(trifluoro methyl)tetrahydro-2H-pyran-2-yl)methyl)phosphonate that was used in next step without purification (40 mg, 88%): $^1$H NMR (400 MHz, CDCl$_3$) δ 4.54-4.50 (m, 1H), 4.25-4.19 (m, 1H), 4.08-3.97 (m, 2H), 3.77 (d, J=6.0 Hz, 3H), 3.73 (d, J=6.0 Hz, 3H), 3.58-3.54 (m, 1H), 1.58 (s, 3H), 2.44-2.16 (m, 2H); $^{19}$F NMR (376.17 MHz, CDCl$_3$) δ −74.36 ppm.

(2R,3S,4R,5S,6R)-2-((dimethoxyphosphoryl)methyl)-6-(trifluoromethyl)tetrahydro-2H-pyran-3,4,5-triyl triacetate: In a 25 mL round bottom flask, dimethyl (((2R,3S,4R,5S,6R)-3,4,5-trihydroxy-6-(trifluoro methyl)tetrahydro-2H-pyran-2-yl)methyl)phosphonate (50 mg, 0.112 mmol) was taken up in pyridine (1.5 mL, Rankem, India) under a nitrogen atmosphere, and the resulting solution was cooled to 0° C. Acetic anhydride (0.8 mL, 8.48 mmol, Rankem, India) was added at the same temperature. The reaction mixture was warmed to rt and stirred at rt for 16 h under a nitrogen atmosphere. Upon completion of the reaction (TLC, 10% MeOH—CHCl$_3$, R$_f$ 0.4), the reaction mixture was concentrated under reduced pressure. The residue obtained was purified by silica gel (60-120 mesh) column chromatography (elution 50% EtOAc-hexanes) to give (2R,3S,4R,5S,6R)-2-((dimethoxyphosphoryl)methyl)-6-(trifluoromethyl)tetrahydro-2H-pyran-3,4,5-triyl triacetate as a gum (50 mg, 72.4%): $^1$H NMR (400 MHz, CDCl$_3$) δ 5.69 (t, J=2.7 Hz, 1H), 5.43-5.37 (m, 1H), 5.07 (dd, J=9.6, 3.3 Hz, 1H), 4.89-4.81 (m, 1H), 4.31-4.25 (m, 1H), 3.77 (d, J=1.8 Hz, 3H), 3.74 (d, J=2.7 Hz 3H), 2.15 (s, 3H), 2.08 (s, 3H), 2.01 (s, 3H), 2 Hs were obscured; $^{19}$F NMR (376.17 MHz, CDCl$_3$) δ −73.33 ppm.

(2R,3S,4R,5S,6R)-2-((bis((pivaloyloxy)methoxy)phosphoryl)methyl)-6-(trifluoromethyl)tetrahydro-2H-pyran-3,4,5-triyl triacetate. In a 25 mL round bottom flask, (2R,3S,4R,5S,6R)-2-((dimethoxyphosphoryl)methyl)-6-(trifluoromethyl)tetrahydro-2H-pyran-3,4,5-triyl triacetate (50 mg, 0.35 mmol) was dissolved in CH$_3$CN (2 mL) at rt under nitrogen atmosphere. POM-Cl (89 mg, 0.59 mmol, commercially available from Alfa Asear, India), and NaI (89 mg, 0.35 mmol, 5eq, commercially available from Sigma Aldrich, India) were sequentially added to the above solution at rt under nitrogen atmosphere. The resulting mixture was stirred at rt for 1 h and heated at 70° C. for 12 h. Upon completion of the reaction (TLC, 50% EtOAc in hexane R$_f$ 0.4), the reaction mixture was quenched with saturated Na$_2$S$_2$O$_3$ solution (5 mL). The mixture was diluted with water (10 mL) and extracted with EtOAc (2×10 mL). The combined organic extracts were washed with water, brine, dried over anhydrous Na$_2$SO$_4$ and concentrated under reduced pressure. The residue obtained was purified by silica gel (60-120 mesh) column chromatography (gradient elution 30-50% EtOAc-hexanes) to give (2S,3S,4R,5S,6R)-2-((bis((pivaloyl-oxy)methoxy)phosphoryl)methyl)-6-(trifluoromethyl)tetrahydro-2H-pyran-3,4,5-triyl triacetate as a oil (7 mg, 9.7%): $^1$H NMR (400 MHz, CDCl$_3$) δ 5.72-5.62 (m, 5H), 5.39-5.38 (m, 1H), 5.05 (dd, J=9.6, 3.2 Hz 1H), 4.78-4.62 (m, 1H), 4.29 (m, 1H), 2.32-2.19 (m, 2H), 2.13 (s, 3H), 2.10 (s, 3H), 2.01 (s, 3H), 1.23 (s, 18H); $^{19}$F NMR (376.17 MHz, CDCl$_3$) δ −72.31 ppm.

Example 4

(2R,3R,4S,5S,6S)-2-(acetoxymethyl)-6-((bis((pivaloyloxy)methoxy)phosphoryl)methyl)tetrahydro-2H-pyran-3,4,5-triyl triacetate

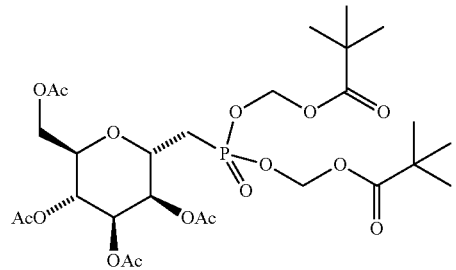

4

Example 4 was synthesized as shown in Scheme 3.

Scheme 3

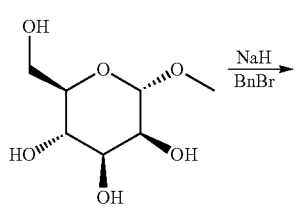

31
-continued

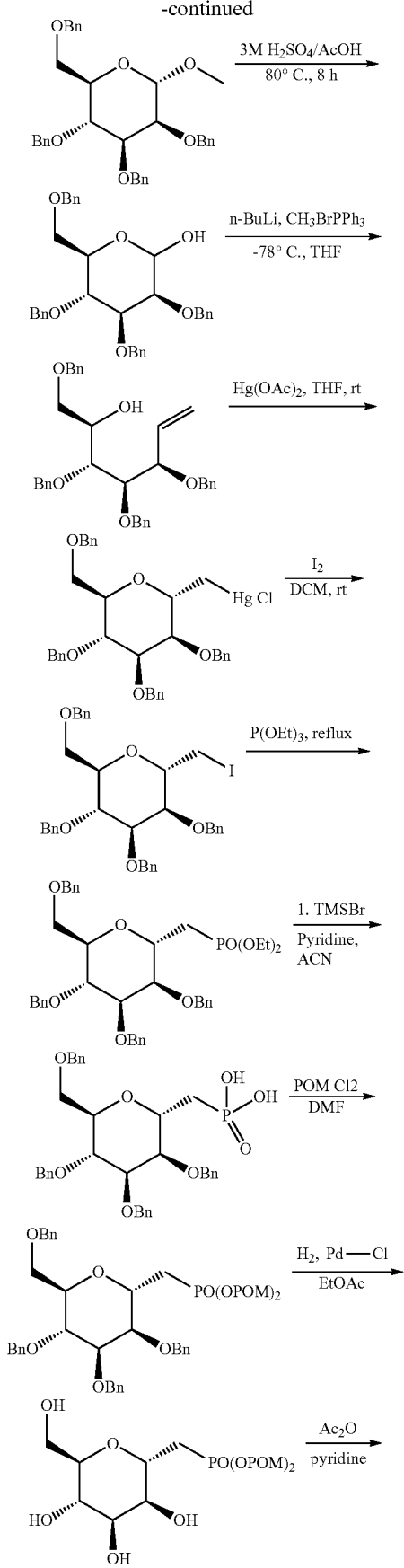

32
-continued

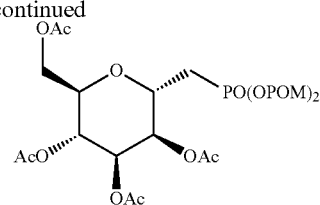

(2R,3R,4S,5S,6S)-3,4,5-tris(benzyloxy)-2-((benzyloxy)methyl)-6-methoxytetrahydro-2H-pyran: To a stirred solution of (2R,3S,4S,5S,6S)-2-(hydroxymethyl)-6-methoxytetrahydro-2H-pyran-3,4,5-triol (15.0 g, 77.2 mmol, 1.0 equiv., commercially available Sigma Aldrich) in dry DMF (250 mL) was added sodium hydride (14.8 g, 309 mmol, 4.0 equiv) at 0° C. under nitrogen atmosphere. The reaction mixture was stirred at the same temperature for 30 minutes and then benzylbromide (38 mL, 309 mmol, 4.0 equiv) was added dropwise. The reaction mixture was stirred at room temperature for 16 hours. The reaction was quenched with MeOH (50 mL) at 0° C. and concentrated in vacuo. Ice cold water (80 mL) was added, the mixture was extracted with EtOAc (2×250 mL), and the combined organic layers were washed with saturated $NaHCO_3$ solution (3×60 mL), dried over anhydrous sodium sulfate, filtered, and concentrated in vacuo. The material thus obtained was purified by silica gel chromatography, eluting with 20% EtOAc in petroleum ether to afford (2R,3R,4S,5S,6S)-3,4,5-tris(benzyloxy)-2-((benzyloxy)methyl)-6-methoxytetrahydro-2H-pyran as a pale yellow oil (28 g, 65%). $^1$H NMR (400 MHz, $CDCl_3$) δ 7.47-7.24 (m, 18H), 7.25-7.15 (m, 2H), 4.92 (d, J=10.8 Hz, 1H), 4.79 (dd, J=17.2, 2.2 Hz, 3H), 4.70 (d, J=12.1 Hz, 1H), 4.67-4.50 (m, 4H), 4.01 (t, J=9.1 Hz, 1H), 3.92 (dd, J=9.3, 3.1 Hz, 1H), 3.86-3.72 (m, 4H), 3.36 (s, 3H). ESI ($M+H_2O$) 572.0, calc for $C_{35}H_{38}O_6$ 554.3.

(3S,4S,5R,6R)-3,4,5-tris(benzyloxy)-6-((benzyloxy)methyl)tetrahydro-2H-pyran-2-ol: To a solution of (2R,3R,4S,5S,6S)-3,4,5-tris(benzyloxy)-2-((benzyloxy)methyl)-6-methoxytetrahydro-2H-pyran (28.0 g, 50.5 mmol, 1.0 equiv) in acetic acid (480 mL), was added 3M $H_2SO_4$ (120 mL, aqueous) at 0° C. The reaction was heated at 80° C. for 10 hours, cooled to room temperature, and then neutralized with saturated aqueous potassium carbonate solution. The mixture was then extracted with DCM (3×1000 mL). The combined organic layers were dried over anhydrous sodium sulfate, filtered, and concentrated in vacuo. The material thus obtained was purified by silica gel chromatography, eluting with 30% EtOAc in petroleum ether, to give (3S,4S,5R,6R)-3,4,5-tris(benzyloxy)-6-((benzyloxy)methyl)tetrahydro-2H-pyran-2-ol as a pale yellow oil (15.0 g, 54%). $^1$H NMR (300 MHz, DMSO-$d_6$) δ 7.38-7.17 (m, 20H), 6.61 (d, J=4.4 Hz, 1H), 5.14-5.07 (m, 1H), 4.77 (t, J=8.5 Hz, 3H), 4.71-4.38 (m, 6H), 3.80 (dp, J=22.8, 9.1, 8.3 Hz, 3H), 3.68-3.53 (m, 2H). ESI ($M+H_2O$) 558.2; calc for $C_{34}H_{36}O_6$ 540.3.

(2R,3R,4R,5R)-1,3,4,5-tetrakis(benzyloxy)hept-6-en-2-ol: Under nitrogen atmosphere, to a stirred solution of methyl triphenylphosphonium bromide (18.4 g, 51.2 mmol, 3.1 equiv) in dry THF (120 mL), was added n-BuLi (19.9 mL, 2.5 M in hexane, 3.0 equiv) dropwise over a period of 1 hour at −78° C. In a separate flask, a solution of (3S,4S,5R,6R)-3,4,5-tris(benzyloxy)-6-((benzyloxy)methyl)tetrahydro-2H-pyran-2-ol (9.0 g, 16.6 mmol, 1.0 equiv) in dry THF (40 mL) was added n-BuLi (7.3 mL, 2.5 M in hexane, 1.1 equiv) dropwise over a period of 10 minutes at −78° C. After 10 minutes, the ylide solution was added to the reaction mixture via cannula at −78° C. The reaction mixture was stirred at the same temperature for 2 hours and then slowly warmed to room temperature and stirred for 16 hours. The reaction was then quenched with saturated aqueous ammonium chloride solution (40 mL) and then extracted with EtOAc (2×250 mL). The combined organic layers were washed with saturated aqueous sodium chloride solution (80 mL), dried over anhydrous sodium sulfate, filtered, and concentrated in vacuo. The material thus obtained was purified by silica gel chromatography, eluting with 20% EtOAc in petroleum ether to give (2R,3R,4R,5R)-1,3,4,5-tetrakis(benzyloxy)hept-6-en-2-ol as a pale yellow oil (2.5 g, 28%). $^1$H NMR (400 MHz, CDCl$_3$) δ 7.43-7.16 (m, 20H), 6.08-5.91 (m, 1H), 5.50-5.38 (m, 2H), 4.77-4.68 (m, 1H), 4.68-4.58 (m, 2H), 4.58-4.52 (m, 1H), 4.52-4.43 (m, 4H), 4.25 (d, J=11.6 Hz, 1H), 4.12 (t, J=7.5 Hz, 1H), 4.02 (ddd, J=7.5, 5.5, 3.5 Hz, 1H), 3.88 (ddd, J=7.6, 5.4, 3.1 Hz, 2H), 3.65 (dd, J=9.6, 3.4 Hz, 1H), 3.58 (dd, J=9.6, 5.4 Hz, 1H). ESI (M+H$_2$O) 556.2; calc for C$_{35}$H$_{38}$O$_6$ 538.3

(((2S,3S,4S,5R,6R)-3,4,5-tris(benzyloxy)-6-((benzyloxy)methyl)tetrahydro-2H-pyran-2-yl)methyl)mercury(II) chloride: To a suspension of Hg(OAc)$_2$ (0.88 g, 2.8 mmol, 1.0 equiv) in dry THF (50 mL) under nitrogen atmosphere was added (2R,3R,4R,5R)-1,3,4,5-tetrakis(benzyloxy)hept-6-en-2-ol (1.5 g, 2.78 mmol, 1.0 equiv) dissolved in 20 mL of dry THF. The reaction was stirred at room temperature for 16 hours and then a saturated aqueous solution of potassium chloride (0.50 g, 4.5 mmol, 1.6 equiv) was added. After 30 minutes, the reaction mixture was diluted with EtOAc (80 mL), washed with water (20 mL), dried over anhydrous sodium sulfate, filtered, and concentrated in vacuo. The material thus obtained was purified by silica gel chromatography, eluting with 30% EtOAc in petroleum ether, to give (((2S,3S,4S,5R,6R)-3,4,5-tris(benzyloxy)-6-((benzyloxy)methyl)tetrahydro-2H-pyran-2-yl)methyl)mercury(II) chloride as a pale yellow oil (1.5 g, 72%). $^1$H NMR (300 MHz, CDCl$_3$) δ 7.45-7.15 (m, 20H), 4.62-4.39 (m, 7H), 4.33 (d, J=11.9 Hz, 1H), 4.24-4.11 (m, 1H), 4.08 (ddd, J=7.7, 5.9, 2.2 Hz, 1H), 3.89-3.76 (m, 2H), 3.72 (dd, J=4.2, 2.3 Hz, 1H), 3.68-3.57 (m, 1H), 3.39 (dd, J=8.5, 2.9 Hz, 1H), 2.18-1.96 (m, 2H). ESI (M+H$_2$O) 792.0; calc for C$_{35}$H$_{37}$ClHgO$_5$ 774.2.

(2R,3R,4S,5S,6S)-3,4,5-tris(benzyloxy)-2-((benzyloxy)methyl)-6-(iodomethyl)tetrahydro-2H-pyran: Iodine (0.36 g, 14.4 mmol, 1.1 equiv) dissolved in dry DCM (20 mL) was added to a solution of (((2S,3S,4S,5R,6R)-3,4,5-tris(benzyloxy)-6-((benzyloxy)methyl)tetrahydro-2H-pyran-2-yl)methyl)mercury(II) chloride (1.0 g, 12.9 mmol, 1.0 equiv) in dry DCM (30 mL). The reaction mixture was stirred at room temperature for 16 hours and then quenched with saturated aqueous sodium thiosulfate solution (50 mL). The biphasic mixture was separated and then the organic layer was washed with saturated aqueous sodium chloride solution (10 mL) and then with water (10 mL). The organic layer was then dried over anhydrous sodium sulfate, filtered, and concentrated in vacuo. The material thus obtained was purified by silica gel chromatography, eluting with 30% EtOAc in petroleum ether, to give (2R,3R,4S,5S,6S)-3,4,5-tris(benzyloxy)-2-((benzyloxy)methyl)-6-(iodomethyl)tetrahydro-2H-pyran as a colorless oil (0.7 g, 82%). $^1$H NMR (300 MHz, CDCl$_3$) δ 7.44-7.22 (m, 18H), 7.17 (dd, J=6.6, 3.0 Hz, 2H), 5.09 (d, J=11.3 Hz, 1H), 4.92-4.67 (m, 4H), 4.67-4.47 (m, 3H), 4.21 (dd, J=2.8, 1.1 Hz, 1H), 3.90 (t, J=9.5 Hz, 1H), 3.76 (dd, J=11.0, 1.9 Hz, 1H), 3.71-3.60 (m, 2H), 3.57 (t, J=6.9 Hz, 1H), 3.53-3.45 (m, 1H), 3.35-3.24 (m, 2H). ESI (M+H$_2$O) 682.2; calc for C$_{35}$H$_{37}$IO$_5$ 664.2.

Diethyl (((2S,3S,4S,5R,6R)-3,4,5-tris(benzyloxy)-6-((benzyloxy)methyl)tetrahydro-2H-pyran-2-yl)methyl)phosphonate: A solution of (2R,3R,4S,5S,6S)-3,4,5-tris(benzyloxy)-2-((benzyloxy)methyl)-6-(iodomethyl)tetrahydro-2H-pyran (0.7 g, 0.75 mmol, 1.0 equiv) in anhydrous triethyl phosphite (9.0 mL) was heated to 160° C. in a 50 mL sealed tube for 16 hours. The solvent was removed using a Kugelrohr distillation setup, and the material thus obtained was purified by silica gel chromatography, eluting with 50% EtOAc in petroleum ether, to give diethyl (((2S,3S,4S,5R,6R)-3,4,5-tris(benzyloxy)-6-((benzyloxy)methyl)tetrahydro-2H-pyran-2-yl)methyl)phosphonate as a pale yellow oil (0.5 g, 70%). $^1$H NMR (300 MHz, CDCl$_3$) δ 7.52-6.98 (m, 20H), 4.77-4.66 (m, 1H), 4.63 (d, J=6.2 Hz, 2H), 4.60-4.42 (m, 6H), 4.16-3.99 (m, 4H), 3.91 (dq, J=8.1, 5.1, 3.9 Hz, 1H), 3.88-3.82 (m, 1H), 3.78 (q, J=4.0 Hz, 4H), 2.25-1.95 (m, 2H), 1.33-1.22 (m, 6H). ESI (M+1) 675.2; calc for C$_{39}$H$_{47}$O$_8$P 674.3.

(((2S,3S,4S,5R,6R)-3,4,5-tris(benzyloxy)-6-((benzyloxy)methyl)tetrahydro-2H-pyran-2-yl)methyl)phosphonic acid: To a solution of (((2S,3S,4S,5R,6R)-3,4,5-tris(benzyloxy)-6-((benzyloxy)methyl)tetrahydro-2H-pyran-2-yl)methyl)phosphonate (0.6 g, 0.89 mmol, 1.0 equiv) in dry acetonitrile (60 mL) was added pyridine (1.1 mL, 10.2 mmol, 11.5 equiv) at 0° C. under argon atmosphere. TMSBr (2.5 mL, 17.7 mmol, 20 equiv) dissolved in dry acetonitrile (25 mL) was added dropwise to the reaction mixture at 0° C. which was stirred for 10 minutes and then warmed to room temperature and stirred for 3 hours. The volatiles were removed in vacuo (bath temperature <15° C.) to give an oil. Ice cold water (20 mL) was added, and the organic material was extracted into DCM (2×80 mL). The combined organic layers were dried over anhydrous sodium sulfate, filtered, and concentrated in vacuo (bath temp <15° C.) to give ((((2S,3S,4S,5R,6R)-3,4,5-tris(benzyloxy)-6-((benzyloxy)methyl)tetrahydro-2H-pyran-2-yl)methyl)phosphonic acid as a pale green solid (0.50 g). The material thus obtained was used without further purification. ESI (M+1) m/z: 619.0; calc for C$_{35}$H$_{39}$O$_8$P 618.2.

(((((2S,3S,4S,5R,6R)-3,4,5-Tris(benzyloxy)-6-((benzyloxy)methyl)tetrahydro-2H-pyran-2-yl)methyl)phosphoryl)bis(oxy))bis(methylene)bis(2,2-dimethylpropanoate): To a stirred solution of (((2S,3S,4S,5R,6R)-3,4,5-tris(benzyloxy)-6-((benzyloxy)methyl)tetrahydro-2H-pyran-2-yl)methyl)phosphonic acid (0.5 g, 8.0 mmol, 1.0 equiv) and a catalytic amount of DMAP in dry DMF (20 mL), was added triethylamine (0.3 mL, 2.4 mmol, 3.0 equiv) followed by POMCl (1.2 mL, 8.0 mmol, 10.0 equiv) at room temperature. The mixture was heated to 70° C. for 2 hours and then additional triethylamine (1.5 equiv) and POMCl (5.0 equiv) were added. The mixture was stirred at 70° C. for an additional 2 hours, and then triethylamine (1.5 equiv) and POMCl (5.0 equiv) were added again. The mixture was stirred at 70° C. for a final 2 hours, cooled to room temperature, and then stirred for 16 hours. Et$_2$O (20 mL) was added and the reaction mixture was washed with water (10 mL) and saturated aqueous sodium bicarbonate solution (10 mL). The organic layer was then dried over anhydrous sodium sulfate, filtered, and concentrated in vacuo. The material thus obtained was purified by silica gel chromatography, eluting with 30% EtOAc in petroleum ether, to give (((((2S,3S,4S,5R,6R)-3,4,5-tris(benzyloxy)-6-((benzyloxy)methyl)tetrahydro-2H-pyran-2-yl)methyl)phosphoryl)bis(oxy))bis(methylene)bis(2,2-dimethylpropanoate) as a pale yellow oil. (0.38 g, 55%). $^1$H NMR (400 MHz, CDCl$_3$) δ 7.39-7.16 (m, 20H), 5.71-5.55 (m, 4H), 4.66-4.36 (m, 9H), 3.91 (q, J=5.1 Hz, 1H), 3.87-3.79 (m, 2H), 3.75 (td, J=9.7, 3.7 Hz, 2H), 3.69 (dd, J=6.4, 2.8 Hz, 1H), 2.39-2.22 (m, 1H), 2.20-2.05 (m, 1H), 1.21 (s, 18H). ESI (M+1) 847.0; calc for C$_{47}$H$_{59}$O$_{12}$P 846.4.

(((((2S,3S,4S,5S,6R)-3,4,5-trihydroxy-6-(hydroxymethyl)tetrahydro-2H-pyran-2-yl)methyl)phosphoryl)bis(oxy))bis(methylene)bis(2,2-dimethylpropanoate): To a solution of (((((2S,3S,4S,5R,6R)-3,4,5-tris(benzyloxy)-6-((benzyloxy)methyl)tetrahydro-2H-pyran-2-yl)methyl)phosphoryl)bis(oxy))bis(methylene)bis(2,2-dimethylpropanoate) (0.38 g, 0.45 mmol, 1.0 equiv) in EtOAc (70 mL) was added 10% Pd/C (120 mg) and 20% Pd(OH)$_2$ (120 mg) under nitrogen atmosphere. The suspension was then placed under 1 atm hydrogen (bladder) and stirred for 6 hours. The reaction mixture was filtered through a pad of Celite® filter aid and then the filtration material was washed with EtOAc (60 mL) followed by MeOH (30 mL). The filtrate was concentrated in vacuo to afford a residue which was washed with dry n-hexane to give (((((2S,3S,4S,5S,6R)-3,4,5-trihydroxy-6-(hydroxymethyl)tetrahydro-2H-pyran-2-yl)methyl)phosphoryl)bis(oxy))bis(methylene)bis(2,2-dimethylpropanoate) as an off-white solid (0.18 g, 82%). $^1$H NMR (400 MHz, DMSO-d$_6$) δ 5.69-5.52 (m, 4H), 4.85-4.73 (m, 2H), 4.68 (d, J=5.4 Hz, 1H), 4.28 (t, J=5.8 Hz, 1H), 4.01 (s, 1H), 3.71-3.45 (m, 4H), 3.45-3.37 (m, 2H), 2.27 (s, 2H), 1.18 (d, J=0.7 Hz, 18H). ESI (M+1) 487.2; calc for $C_{19}H_{35}O_{12}P$ 486.2.

(2R,3R,4S,5S,6S)-2-(Acetoxymethyl)-6-((bis((pivaloyloxy)methoxy)phosphoryl)methyl)tetrahydro-2H-pyran-3,4,5-triyl triacetate: To a stirred solution of (((((2S,3S,4S,5S,6R)-3,4,5-trihydroxy-6-(hydroxymethyl)tetrahydro-2H-pyran-2-yl)methyl)phosphoryl)bis(oxy))bis(methylene)bis(2,2-dimethylpropanoate) (0.18 g, 0.37 mmol, 1.0 equiv) and a catalytic amount of DMAP in dry DCM (18 mL), was added pyridine (1.8 mL) at room temperature. The resulting mixture was stirred for 5 minutes. The reaction mixture was then cooled to 0° C. and acetic anhydride (0.9 mL) was added. The resulting solution was stirred at room temperature for 16 hours and then the reaction was cooled back to 0° C. before MeOH (2 mL) was added. The volatiles were then removed in vacuo, and the resulting product was purified by silica gel chromatography, eluting with 40% EtOAc in petroleum ether, to give (2R,3R,4S,5S,6S)-2-(acetoxymethyl)-6-((bis((pivaloyloxy)methoxy)phosphoryl)methyl)tetrahydro-2H-pyran-3,4,5-triyl triacetate as a colorless semi solid (0.15 g, 24%). $^1$H NMR (400 MHz, CDCl$_3$) δ 5.78-5.64 (m, 4H), 5.26 (dd, J=7.5, 3.2 Hz, 1H), 5.20-5.09 (m, 2H), 4.49-4.36 (m, 2H), 4.26-4.18 (m, 1H), 4.02 (td, J=6.3, 3.5 Hz, 1H), 2.40-2.15 (m, 2H), 2.13 (s, 3H), 2.12 (s, 3H), 2.11 (s, 3H), 2.08 (s, 3H), 1.26 (s, 18H). MS (ESI (M+H$_2$O) 672.2; calc for $C_{27}H_{43}O_{16}P$ 654.2.

Example 5

(((((2S,3R,4R,5S,6R)-3-acetamido-4,5-diacetoxy-6-(acetoxymethyl)tetrahydro-2H-pyran-2-yl)methyl)phosphoryl)bis(oxy))bis(methylene)bis(2,2-dimethylpropanoate)

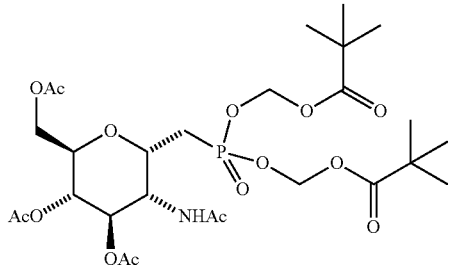

Example 5 was prepared as shown in Scheme 4.

Scheme 4

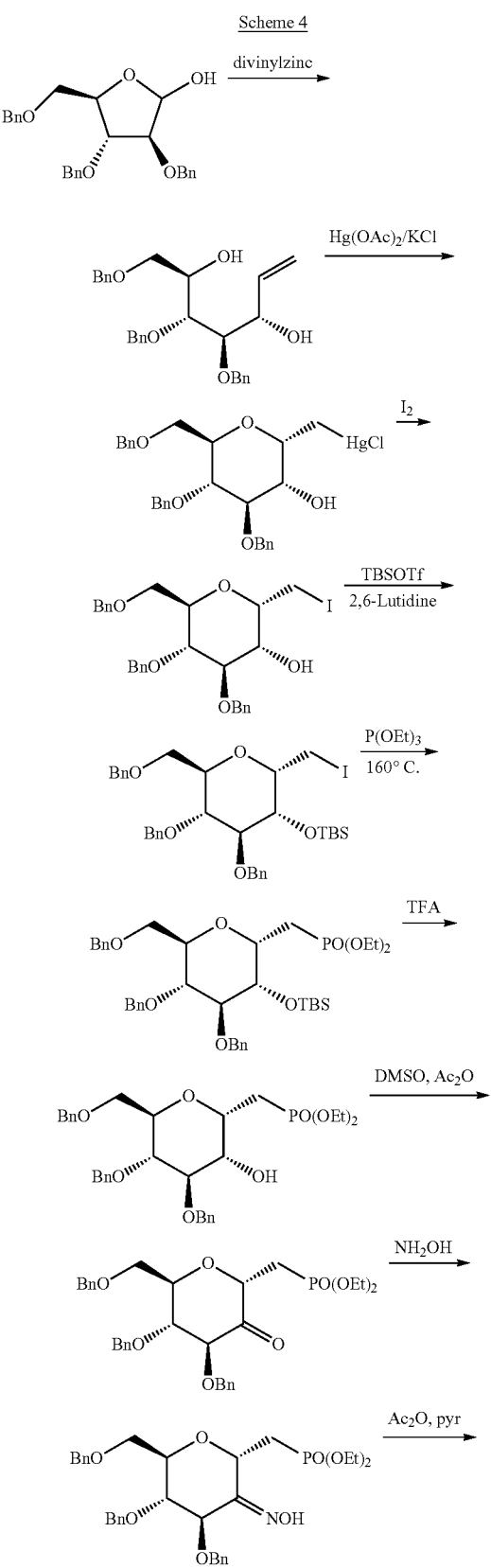

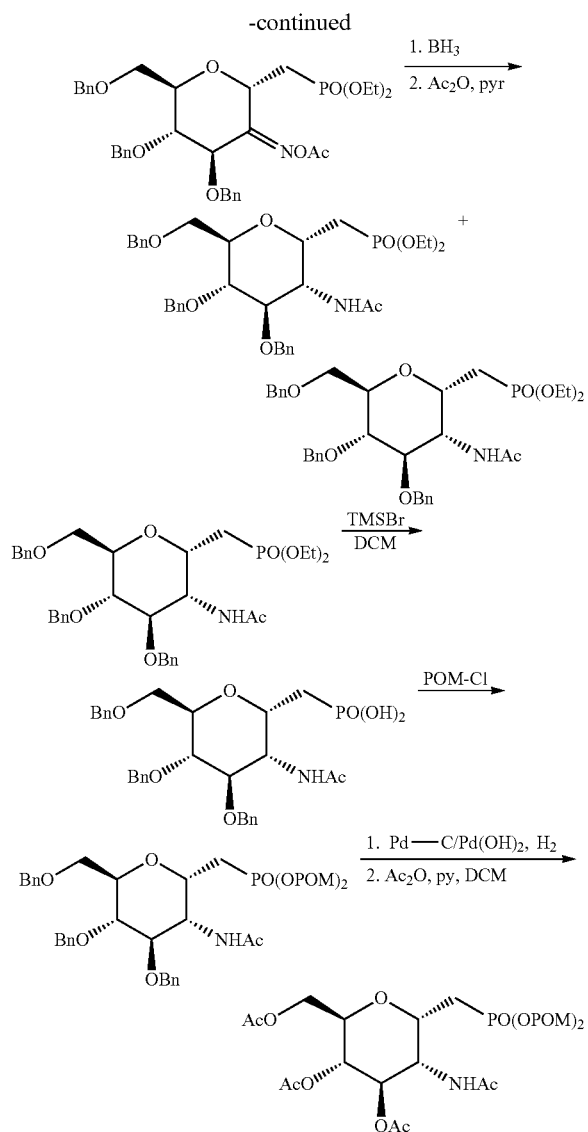

(2R,3R,4R,5S)-1,3,4-Tris(benzyloxy)hept-6-ene-2,5-diol: To a 1M solution in THF of vinylmagnesium bromide (161.7 mL, 161.7 mmol, 4.0 equiv., commercially available from Sigma Aldrich) was added a solution of $ZnBr_2$ (18.2 g, 80.9 mmol, 2.0 equiv) in dry THF (85 mL) at 0° C. under nitrogen atmosphere. The reaction mixture was allowed to warm to room temperature and stirred for 45 minutes. A solution of 2,3,5-tri-O-benzyl-α-D-arabinofuranose (17.0 g, 40.4 mmol, 1.0 equiv., commercially available from Carbosynth Ltd.) in dry THF (170 mL) was added via cannula to the organometallic reagent at 0-5° C. This mixture was then warmed to room temperature and stirred for 16 hours. The reaction mixture was cooled to 0° C. and then quenched with saturated aqueous ammonium chloride solution. The organic phase was diluted with DCM (100 mL) and sequentially washed with 5% aqueous HCl (100 mL), saturated aqueous sodium bicarbonate solution (100 mL) and water (100 mL). The organic layer was then dried over anhydrous sodium sulfate, filtered and concentrated in vacuo to give an oil, which was then purified by silica gel column chromatography, eluting with 15% EtOAc in petroleum ether, to give (2R,3R,4R,5S)-1,3,4-tris(benzyloxy)hept-6-ene-2,5-diol as a pale yellow oil (17.4 g, 96%). $^1$H NMR (400 MHz, $CDCl_3$) δ 7.40-7.22 (m, 15H), 5.93 (ddd, J=17.2, 10.5, 5.6 Hz, 1H), 5.35 (dt, J=17.3, 1.6 Hz, 1H), 5.20 (dt, J=10.5, 1.5 Hz, 1H), 4.76-4.54 (m, 6H), 4.42 (ddt, J=5.4, 3.9, 1.6 Hz, 1H), 4.07 (ddd, J=6.9, 5.4, 3.8 Hz, 1H), 3.78-3.61 (m, 4H). ESI (M+23) 471.0; calc for $C_{28}H_{32}O_5$ 448.2.

(((2S,3R,4R,5R,6R)-4,5-Bis(benzyloxy)-6-((benzyloxy)methyl)-3-hydroxytetrahydro-2H-pyran-2-yl)methyl)mercury(II) chloride: To a suspension of $Hg(OAc)_2$ (12.4 g, 38.8 mmol, 1.0 equiv) in dry THF (174 mL), under nitrogen, was added a solution of (2R,3R,4R,5S)-1,3,4-tris(benzyloxy)hept-6-ene-2,5-diol (17.4 g, 38.8 mmol, 1.0 equiv) in dry THF (87 mL). The reaction mixture was stirred at room temperature for 16 hours and then a solution of KCl (4.3 g, 58.2 mmol, 1.5 equiv) in water (20 mL) was added. After 30 minutes, the reaction mixture was diluted with EtOAc (150 mL) and then washed with water (2×100 mL). The organic phase was then dried over anhydrous sodium sulfate, filtered, and concentrated in vacuo to give an oil. This oil was purified by silica gel chromatography, eluting with 20% EtOAc in hexane, to give (((2S,3R,4R,5R,6R)-4,5-bis(benzyloxy)-6-((benzyloxy)methyl)-3-hydroxytetrahydro-2H-pyran-2-yl)methyl)mercury(II) chloride as a pale yellow oil (22.6 g, 85%). $^1$H NMR (400 MHz, $CDCl_3$) δ 7.37-7.29 (m, 11H), 7.27-7.24 (m, 2H), 7.23-7.19 (m, 2H), 4.62-4.48 (m, 6H), 4.37 (dd, J=7.1, 3.7 Hz, 1H), 4.15 (dt, J=6.3, 4.1 Hz, 1H), 3.82 (dd, J=10.1, 6.7 Hz, 1H), 3.72 (q, J=2.8, 1.9 Hz, 1H), 3.65-3.59 (m, 2H), 3.53-3.47 (m, 2H), 2.06-2.00 (m, 1H), 1.77 (dd, J=12.1, 3.8 Hz, 1H). ESI (M+1-Cl) 647.1; calc for $C_{28}H_{31}ClHgO_5$ 684.2.

(2S,3R,4R,5R,6R)-4,5-Bis(benzyloxy)-6-((benzyloxy)methyl)-2-(iodomethyl)tetrahydro-2H-pyran-3-ol: A solution of iodine (3.36 g, 13.2 mmol, 1.2 equiv) in DCM (168 mL) was added to a solution of (((2S,3R,4R,5R,6R)-4,5-bis(benzyloxy)-6-((benzyloxy)methyl)-3-hydroxytetrahydro-2H-pyran-2-yl)methyl)mercury(II) chloride (7.5 g, 11.0 mmol, 1.0 equiv) in dry DCM (26 mL) under nitrogen atmosphere. The mixture was stirred for 16 hours and then the reaction was quenched with aqueous sodium thiosulfate solution (20 g in 50 mL water). The mixture was stirred until colorless, the layers were separated, and the organic layer was washed with saturated sodium chloride solution (75 mL) and then water (75 mL). The organic phase was dried over anhydrous sodium sulfate, filtered, and concentrated in vacuo. The material thus obtained was then purified by silica gel chromatography, eluting with 15% EtOAc in petroleum ether, to give (2S,3R,4R,5R,6R)-4,5-bis(benzyloxy)-6-((benzyloxy)methyl)-2-(iodomethyl)tetrahydro-2H-pyran-3-ol as a colorless oil (5.1 g, 81%). $^1$H NMR (300 MHz, $CDCl_3$) δ 7.40-7.20 (m, 15H), 4.65-4.49 (m, 6H), 4.12 (td, J=5.5, 2.9 Hz, 1H), 4.02 (ddd, J=8.3, 5.8, 2.5 Hz, 1H), 3.85 (dd, J=10.1, 6.0 Hz, 2H), 3.74 (dt, J=10.4, 5.1 Hz, 2H), 3.63 (t, J=3.8 Hz, 1H), 3.40 (dd, J=10.3, 5.8 Hz, 1H), 3.29 (dd, J=10.5, 8.5 Hz, 1H), 3.11 (d, J=9.2 Hz, 1H). ESI (M+23) 597.0; calc for $C_{28}H_{31}IO_5$ 574.1.

(((2S,3R,4S,5R,6R)-4,5-Bis(benzyloxy)-6-((benzyloxy)methyl)-2-(iodomethyl)tetrahydro-2H-pyran-3-yl)oxy)(tert-butyl)dimethylsilane: To a solution of (2S,3R,4R,5R,6R)-4,5-bis(benzyloxy)-6-((benzyloxy)methyl)-2-(iodomethyl)tetrahydro-2H-pyran-3-ol (1.0 g, 1.74 mmol, 1.0 equiv) in dry DCM (10 mL) under nitrogen atmosphere, was added 2,6-lutidine (0.41 mL, 3.5 mmol, 2.0 equiv) at room temperature. The resulting mixture was stirred for 5 minutes. The reaction was cooled to 0° C. and TBSOTf (0.6 mL, 2.6 mmol, 1.5 equiv) was added dropwise. The mixture was then slowly allowed to warm to room temperature. After 1 hour, the mixture was diluted with DCM (20 mL) and washed with water (2×20 mL). The organic layer was dried over $Na_2SO_4$ and over anhydrous sodium sulfate, filtered, and concentrated in vacuo to give an oil. The oil was then purified by silica gel chromatography, eluting with 5% EtOAc in petroleum ether to give (((2S,3R,4S,5R,6R)-4,5-bis(benzyloxy)-6-((benzyloxy)methyl)-2-(iodomethyl)tetrahydro-2H-pyran-3-yl)oxy)(tert-butyl)dimethylsilane as a colorless oil (1.05 g, 94%). $^1$H NMR (400 MHz, $CDCl_3$) δ 7.40-7.22 (m, 13H), 7.09-7.04 (m, 2H), 4.90-4.77 (m, 2H), 4.77-4.68 (m, 2H), 4.53 (d, J=12.1 Hz, 1H), 4.47 (d, J=10.7 Hz, 1H), 4.09 (ddd, J=12.2, 5.9, 3.4 Hz, 1H), 3.91 (dd, J=9.2, 5.9 Hz, 1H), 3.81 (dd, J=10.7, 3.2 Hz, 1H), 3.75 (dd, J=10.7, 2.1 Hz, 1H), 3.69 (dd, J=9.9, 8.7 Hz, 1H), 3.63-3.56 (m, 2H), 3.51 (dt, J=9.9, 2.6 Hz, 1H), 3.41 (t, J=11.8 Hz, 1H), 0.91 (s, 9H), 0.09 (s, 3H), 0.07 (s, 3H).

Diethyl (((2S,3R,4S,5R,6R)-4,5-Bis(benzyloxy)-6-((benzyloxy)methyl)-3-((tert-butyldimethylsilyl)oxy)tetrahydro-2H-pyran-2-yl)methyl)phosphonate: A solution of (((2S,3R,4S,5R,6R)-4,5-bis(benzyloxy)-6-((benzyloxy)methyl)-2-(iodomethyl)tetrahydro-2H-pyran-3-yl)oxy)(tert-butyl)dimethylsilane (4.0 g, 5.8 mmol, 1.0 equiv) in anhydrous triethyl phosphite (40 mL) was heated to 160° C. in a 100 mL sealed tube for 16 hours. The solvent was removed in vacuo and the resulting product was purified by silica gel chromatography, eluting with 30% EtOAc in petroleum ether, to give diethyl (((2S,3R,4S,5R,6R)-4,5-bis(benzyloxy)-6-((benzyloxy)methyl)-3-((tert-butyldimethylsilyl)oxy)tetrahydro-2H-pyran-2-yl)methyl)phosphonate as a pale yellow oil (3.36 g, 83%). $^1$H NMR (300 MHz, $CDCl_3$) δ 7.37-7.22 (m, 13H), 7.06 (dd, J=6.6, 3.0 Hz, 2H), 4.90-4.72 (m, 3H), 4.67-4.61 (m, 1H), 4.49 (d, J=4.3 Hz, 1H), 4.46 (d, J=2.9 Hz, 1H), 4.40 (d, J=7.1 Hz, 1H), 4.17-4.03 (m, 4H), 3.93-3.85 (m, 1H), 3.77 (d, J=9.9 Hz, 1H), 3.72-3.61 (m, 3H), 3.55-3.47 (m, 1H), 2.27-2.13 (m, 2H), 1.29 (td, J=7.1, 1.2 Hz, 6H), 0.90 (s, 9H), 0.09 (s, 3H), 0.07 (s, 3H). ESI (M+1) 699.2; calc for $C_{38}H_{55}O_8PSi$ 698.3.

Diethyl (((2S,3R,4R,5R,6R)-4,5-Bis(benzyloxy)-6-((benzyloxy)methyl)-3-hydroxytetrahydro-2H-pyran-2-yl)methyl)phosphonate: A solution of diethyl (((2S,3R,4S,5R,6R)-4,5-bis(benzyloxy)-6-((benzyloxy)methyl)-3-((tert-butyldimethylsilyl)oxy)tetrahydro-2H-pyran-2-yl)methyl)phosphonate (3.3 g, 4.72 mmol, 1.0 equiv) in DCM (50 mL) was cooled to 0° C., and a mixture of trifluoroacetic acid and water (3.3 mL/0.33 mL) was added. The reaction mixture was then stirred at room temperature for 16 hours. The mixture was then sequentially washed with saturated aqueous sodium bicarbonate solution (120 mL) and water (100 mL). The organic layer was dried over anhydrous sodium sulfate, filtered, and concentrated in vacuo. The product thus obtained was purified by silica gel chromatography, eluting with 70% EtOAc in petroleum ether to give diethyl (((2S,3R,4R,5R,6R)-4,5-bis(benzyloxy)-6-((benzyloxy)methyl)-3-hydroxytetrahydro-2H-pyran-2-yl)methyl)phosphonate as a white solid (2.1 g, 76%). $^1$H NMR (300 MHz, $CDCl_3$) δ 7.36-7.22 (m, 15H), 4.66-4.56 (m, 3H), 4.52 (s, 2H), 4.41-4.31 (m, 2H), 4.18-4.00 (m, 4H), 3.87-3.70 (m, 4H), 3.67 (td, J=4.1, 1.5 Hz, 1H), 2.24-2.17 (m, 1H), 2.14 (d, J=6.9 Hz, 1H), 1.82-1.67 (m, 2H), 1.34-1.28 (m, 6H). MS (ESI positive ion) m/z: 585.0 (M+1); calc for $C_{32}H_{41}O_8P$ 584.3.

Diethyl (((2S,4S,5R,6R)-4,5-bis(benzyloxy)-6-((benzyloxy)methyl)-3-oxotetrahydro-2H-pyran-2-yl)methyl)phosphonate: A mixture of (((2S,3R,4R,5R,6R)-4,5-bis(benzyloxy)-6-((benzyloxy)methyl)-3-hydroxytetrahydro-2H-pyran-2-yl)methyl)phosphonate (9.0 g, 15.4 mmol, 1.0 equiv) and DMSO:$Ac_2O$ (67.5 mL, 3:2) was stirred at room temperature for 16 hours. The reaction was quenched by adding ice-cold water (135 mL) and extracted with DCM (2×100 mL). The organic layer was washed with saturated aqueous sodium bicarbonate solution (90 mL) and water to neutrality, dried over sodium sulfate, filtered, and concentrated in vacuo to give the product. This material was purified by silica gel chromatography, eluting with 50% EtOAc in hexane, to give diethyl (((2S,4S,5R,6R)-4,5-bis(benzyloxy)-6-((benzyloxy)methyl)-3-oxotetrahydro-2H-pyran-2-yl)methyl)phosphonate as a colorless oil (5.4 g, 60%). $^1$H NMR (400 MHz, $CDCl_3$) δ 7.47-7.42 (m, 2H), 7.38-7.24 (m, 13H), 7.21 (dt, J=6.8, 2.7 Hz, 2H), 5.00 (d, J=11.4 Hz, 1H), 4.83 (d, J=11.2 Hz, 1H), 4.68-4.59 (m, 3H), 4.54-4.47 (m, 2H), 4.39 (d, J=12.0 Hz, 1H), 4.18-3.96 (m, 4H), 3.68 (dd, J=10.6, 2.6 Hz, 1H), 3.62 (dd, J=10.6, 3.8 Hz, 1H), 2.26 (dqd, J=17.4, 15.4, 6.5 Hz, 2H), 1.30 (q, J=6.9 Hz, 6H). MS (ESI positive ion) m/z: 583.0 (M+1). calc for $C_{32}H_{39}O_8P$ 582.2.

Diethyl (((2S,4R,5S,6R)-4,5-bis(benzyloxy)-6-((benzyloxy)methyl)-3-(hydroxyimino)tetrahydro-2H-pyran-2-yl)methyl)phosphonate: A solution of diethyl (((2 S,4S,5R,6R)-4,5-bis(benzyloxy)-6-((benzyloxy)methyl)-3-oxotetrahydro-2H-pyran-2-yl)methyl)phosphonate (1.3 g, 2.23 mmol, 1.0 equiv) in THF/MeOH (42 mL, 1:1) was treated with a buffer solution (17.68 mL) prepared with 15 g of AcONa.3$H_2O$ and 7.5 g of $NH_2OH.HCl$. The pH was then adjusted to 4.5 by dropwise addition of acetic acid. After 1 hour, the mixture was extracted with DCM (3×30 mL), and the organic layer was washed sequentially with water (50 mL), saturated aqueous sodium bicarbonate solution (75 mL) and finally with water to neutrality. The organic layer was dried over anhydrous sodium sulfate, filtered, and concentrated in vacuo. The product thus obtained was purified by silica gel chromatography, eluting with 60% EtOAc in hexane to give diethyl (((2S,4R,5S,6R)-4,5-bis(benzyloxy)-6-((benzyloxy)methyl)-3-(hydroxyimino)tetrahydro-2H-pyran-2-yl)methyl)phosphonate (0.98 g, 74%) as a mixture of E and Z isomers as a white solid. NMR data refers to the more abundant isomer. $^1$H NMR (400 MHz, DMSO-$d_6$) δ 11.36 (d, J=1.1 Hz, 1H), 7.39-7.25 (m, 13H), 7.21 (dd, J=7.6, 2.0 Hz, 2H), 5.21 (td, J=10.6, 3.2 Hz, 1H), 4.73 (d, J=12.0 Hz, 1H), 4.64 (d, J=11.5 Hz, 1H), 4.57-4.47 (m, 4H), 4.40 (d, J=6.6 Hz, 1H), 4.04-3.91 (m, 5H), 3.71 (t, J=6.0 Hz, 1H), 3.60 (dd, J=10.1, 4.9 Hz, 1H), 3.53 (dd, J=10.2, 4.7 Hz, 1H), 2.70-2.53 (m, 1H), 2.11 (ddd, J=19.4, 15.7, 3.8 Hz, 1H), 1.19 (qd, J=7.1, 1.1 Hz, 6H). ESI (M+1) 598.0; calc for $C_{32}H_{40}NO_8P$ 597.3.

Diethyl (((2S,4R,5S,6R)-3-(acetoxyimino)-4,5-bis(benzyloxy)-6-((benzyloxy)methyl)tetrahydro-2H-pyran-2-yl)methyl)phosphonate: To a solution of diethyl (((2S,4R,5S,6R)-4,5-bis(benzyloxy)-6-((benzyloxy)methyl)-3-(hydroxyimino)tetrahydro-2H-pyran-2-yl)methyl)phosphonate (2.0 g, 3.35 mmol, 1.0 equiv) in dry DCM (40 mL) was added catalytic DMAP, pyridine (2.1 mL, 26.8 mmol, 8.0 equiv) and $Ac_2O$ (1.26 mL, 13.4 mmol, 4.0 equiv) slowly. The mixture was stirred at room temperature for 16 hours and then the concentrated in vacuo. The product thus obtained was then purified by silica gel chromatography, eluting with MeOH:acetone:chloroform:petroleum ether (0.5:0.5:1:8), to give diethyl (((2 S,4R,5 S,6R)-3-(acetoxyimino)-4,5-bis(benzyloxy)-6-((benzyloxy)methyl)tetrahydro-2H-pyran-2-yl)methyl)phosphonate as a colorless oil (1.5 g, 70%). $^1$H NMR (400 MHz, $CDCl_3$) δ 7.32 (dddd, J=21.0, 10.3, 8.1, 6.0 Hz, 13H), 7.20 (ddq, J=8.2, 5.4, 3.0 Hz, 2H), 5.48-5.38 (m, 1H), 4.90 (d, J=11.6 Hz, 1H), 4.72 (d, J=11.5 Hz, 1H), 4.62-4.44 (m, 5H), 4.18-4.02 (m, 4H), 3.95-3.83 (m, 2H), 3.63 (qd, J=10.1, 4.8 Hz, 2H), 2.61-2.46 (m, 1H), 2.26-2.15 (m, 4H), 1.32 (td, J=7.1, 1.9 Hz, 6H). MS ESI (M+1) 639.8; calc for $C_{34}H_{42}NO_9P$ 639.3.

Diethyl (((2S,3R,4R,5S,6R)-3-acetamido-4,5-bis(benzyloxy)-6-((benzyloxy)methyl)tetrahydro-2H-pyran-2-yl)methyl)phosphonate and diethyl (((2S,3S,4R,5S,6R)-3-acetamido-4,5-bis(benzyloxy)-6-((benzyloxy)methyl)tetrahydro-2H-pyran-2-yl)methyl)phosphonate: A solution of diethyl (((2S,4R,5S,6R)-3-(acetoxyimino)-4,5-bis(benzyloxy)-6-((benzyloxy)methyl)tetrahydro-2H-pyran-2-yl)methyl) phosphonate (1.0 g, 1.56 mmol, 1.0 equiv) in dry THF (5 mL) was cooled to 0° C. under nitrogen atmosphere. A solution of BH$_3$.THF (1.0 M, 20 mL, 20.0 mmol) was added slowly. After addition was complete, the reaction mixture was warmed to room temperature and stirred for 16 hours. The mixture was cooled back to 0° C. and 1.5N aqueous HCl solution (75 mL) was added dropwise. The resulting solution was heated to 50° C. for 2 hours and then cooled to room temperature. The resulting mixture was extracted with DCM (3×50 mL), the combined organic extracts were washed with water (100 mL), dried over anhydrous sodium sulfate, and concentrated in vacuo to give the product as a mixture of the gluco and manno isomers, which was taken to the next step without further purification. The above material was dissolved in dry DCM (10 mL) and catalytic DMAP, pyridine (1.1 mL, 13.7 mmol, 8.0 equiv) and Ac$_2$O (0.65 mL, 6.86 mmol, 4.0 equiv) were added. The mixture was stirred at room temperature for 16 hours. The solvent was removed in vacuo and the product thus obtained was purified by silica gel chromatography, eluting with 20 to 45% (5% MeOH in EtOAc) in CHCl$_3$, to give diethyl (((2S,3R,4R,5S,6R)-3-acetamido-4,5-bis(benzyloxy)-6-((benzyloxy)methyl)tetrahydro-2H-pyran-2-yl)methyl)phosphonate (400 mg, 37%) and diethyl (((2S,3S,4R,5S,6R)-3-acetamido-4,5-bis(benzyloxy)-6-((benzyloxy)methyl)tetrahydro-2H-pyran-2-yl)methyl)phosphonate (220 mg, 21%), both as pale yellow oils. Diethyl (((2S,3R,4R,5S,6R)-3-acetamido-4,5-bis(benzyloxy)-6-((benzyloxy)methyl)tetrahydro-2H-pyran-2-yl)methyl)phosphonate. $^1$H NMR (400 MHz, CDCl$_3$) δ 7.39-7.22 (m, 15H), 4.68-4.52 (m, 3H), 4.52-4.38 (m, 4H), 4.22 (q, J=10.0, 8.3 Hz, 2H), 4.16-4.00 (m, 4H), 3.97-3.82 (m, 2H), 3.67 (ddt, J=20.2, 2.9, 1.5 Hz, 2H), 2.01-1.89 (m, 2H), 1.86 (s, 3H), 1.32-1.27 (m, 6H). ESI (M+1) 626.0; cal for C$_{34}$H$_{44}$NO$_8$P 625.3. Diethyl (((2S,3S,4R,5S,6R)-3-acetamido-4,5-bis(benzyloxy)-6-((benzyloxy)methyl)tetrahydro-2H-pyran-2-yl)methyl)phosphonate. $^1$H NMR (400 MHz, CDCl$_3$) δ 7.40-7.21 (m, 15H), 5.93 (d, J=9.2 Hz, 1H), 4.69 (d, J=11.6 Hz, 1H), 4.54 (d, J=16.6 Hz, 3H), 4.49-4.38 (m, 3H), 4.27-4.15 (m, 1H), 4.09 (dtd, J=14.4, 7.2, 3.2 Hz, 4H), 3.95 (t, J=5.0 Hz, 1H), 3.86-3.70 (m, 4H), 2.16-2.02 (m, 2H), 1.90 (s, 3H), 1.35-1.28 (m, 6H). ESI (M+1) 626.0; calc for C$_{34}$H$_{44}$NO$_8$P 625.3.

(((2S,3R,4R,5S,6R)-3-acetamido-4,5-bis(benzyloxy)-6-((benzyloxy)methyl)tetrahydro-2H-pyran-2-yl)methyl) phosphonic acid: To a solution of diethyl(((2S,3R,4R,5S,6R)-3-acetamido-4,5-bis(benzyloxy)-6-((benzyloxy)methyl)tetrahydro-2H-pyran-2-yl)methyl)phosphonate (0.40 g, 0.64 mmol, 1.0 equiv) in dry acetonitrile (23.5 mL) was added pyridine (0.6 mL, 7.36 mmol, 11.5 equiv) at 0° C. under argon atmosphere. Then, anhydrous TMSBr (1.65 mL, 10.2 mmol, 16.0 equiv) dissolved in 16.5 mL of dry acetonitrile was added dropwise at −5 to 0° C. The resulting mixture was stirred for 10 minutes. The resulting reaction mixture was allowed to warm to room temperature 4 hours and then the volatiles were removed in vacuo (bath temperature <15° C.). To the residue was added ice-cold water (10 mL), and the organic material was extracted into DCM (2×10 mL). The organic layer was then dried over anhydrous sodium sulfate, filtered, and concentrated in vacuo (bath temperature <15° C.) to obtain (((2S,3R,4R,5S,6R)-3-acetamido-4,5-bis(benzyloxy)-6-((benzyloxy)methyl)tetrahydro-2H-pyran-2-yl) methyl)phosphonic acid (0.45 g) as a pale green solid. This material was directly taken forward to the next step without purification. ESI (M+1) 570.0; calc for C$_{30}$H$_{36}$NO$_8$P 569.2.

(((((2S,3R,4R,5S,6R)-3-acetamido-4,5-bis(benzyloxy)-6-((benzyloxy)methyl)tetrahydro-2H-pyran-2-yl)methyl) phosphoryl)bis(oxy))bis(methylene)bis(2,2-dimethylpropanoate): To a stirred solution of (((2S,3R,4R,5S,6R)-3-acetamido-4,5-bis(benzyloxy)-6-((benzyloxy)methyl) tetrahydro-2H-pyran-2-yl)methyl)phosphonic acid (0.45 g, 0.79 mmol, 1.0 equiv) and a catalytic amount of DMAP in anhydrous DMF (13.5 mL) was added DIPEA (0.4 mL, 2.38 mmol, 3.0 equiv) at room temperature. POM-Cl (1.14 mL, 7.9 mmol, 10.0 equiv) was added to the reaction mixture, and the reaction was heated at 70° C. for 2 hours. Additional DIPEA (0.2 mL, 1.19 mmol, 1.5 eq) and POM-Cl (0.57 mL, 3.95 mmol, 5.0 equiv) were added at 70° C. after 2 hours and 4 hours. After heating at 70° C. for a total of 6 hours, the reaction mixture was cooled to room temperature and stirred for 16 hours. Diethyl ether (10 mL) was added, and the reaction mixture was washed with water (5 mL), saturated aqueous sodium bicarbonate solution (5 mL) and again with water (5 mL). The organic layer was dried over anhydrous sodium sulfate, filtered, and concentrated in vacuo to give the product. The product thus obtained was purified by silica gel chromatography, eluting with 30% EtOAc in petroleum ether to give (((((2S,3R,4R,5S,6R)-3-acetamido-4,5-bis(benzyloxy)-6-((benzyloxy)methyl)tetrahydro-2H-pyran-2-yl)methyl)phosphoryl)bis(oxy))bis(methylene)bis(2,2-dimethylpropanoate) as a pale green oil (0.25 g, 40%). $^1$H NMR (400 MHz, CDCl$_3$) δ 7.38-7.29 (m, 11H), 7.27-7.21 (m, 4H), 6.67 (d, J=9.7 Hz, 1H), 5.71-5.60 (m, 4H), 4.60 (dd, J=11.5, 9.3 Hz, 3H), 4.43 (dd, J=19.9, 11.6 Hz, 4H), 4.25 (t, J=6.8 Hz, 1H), 4.16 (d, J=9.7 Hz, 1H), 3.91 (dd, J=9.8, 6.5 Hz, 1H), 3.83 (dd, J=9.9, 7.0 Hz, 1H), 3.67 (d, J=3.4 Hz, 1H), 3.59 (dt, J=2.7, 1.2 Hz, 1H), 2.16-2.09 (m, 1H), 2.02-1.94 (m, 1H), 1.85 (s, 3H), 1.21 (d, J=4.8 Hz, 18H). ESI (M+1) 798.0; calc for C$_{42}$H$_{56}$NO$_{12}$P 797.4.

(((((2S,3R,4R,5S,6R)-3-acetamido-4,5-dihydroxy-6-(hydroxymethyl)tetrahydro-2H-pyran-2-yl)methyl)phosphoryl) bis(oxy))bis(methylene)bis(2,2-dimethylpropanoate): To a solution of (((((2S,3R,4R,5S,6R)-3-acetamido-4,5-bis(benzyloxy)-6-((benzyloxy)methyl)tetrahydro-2H-pyran-2-yl) methyl)phosphoryl)bis(oxy))bis(methylene)bis(2,2-dimethylpropanoate) (0.25 g, 0.31 mmol, 1.0 equiv) in EtOAc (12.5 mL) was added 10% Pd/C (25 mg) and 20% Pd(OH)$_2$ (25 mg) under nitrogen atmosphere. The mixture was placed under hydrogen atmosphere (bladder) and stirred for 6 hours. The reaction mixture was filtered through a pad of Celite® filtering agent and the pad was washed with EtOAc (50 mL) and then MeOH (50 mL). The filtrate was concentrated in vacuo to afford the product, which was washed with dry n-hexane to give (((((2S,3R,4R,5S,6R)-3-acetamido-4,5-dihydroxy-6-(hydroxymethyl)tetrahydro-2H-pyran-2-yl)methyl)phosphoryl)bis(oxy))bis(methylene)bis(2,2-dimethylpropanoate) as an off white solid (0.14 g, 85%). $^1$H NMR (400 MHz, CDCl$_3$) δ 7.74 (d, J=7.8 Hz, 1H), 5.59 (tt, J=13.1, 5.3 Hz, 4H), 4.98 (d, J=5.7 Hz, 1H), 4.89 (d, J=5.4 Hz, 1H), 4.37 (t, J=5.8 Hz, 1H), 4.24 (s, 1H), 3.75-3.65 (m, 1H), 3.54 (dt, J=11.7, 6.2 Hz, 2H), 3.45-3.34 (m, 2H), 3.19 (q, J=7.8 Hz, 1H), 2.42-2.23 (m, 1H), 1.92 (d, J=18.2 Hz, 1H), 1.83 (s, 3H), 1.17 (s, 18H). ESI (M+1) 528.0; calc for C$_{21}$H$_{38}$NO$_{12}$P 527.2.

(((((2S,3R,4R,5S,6R)-3-acetamido-4,5-diacetoxy-6-(acetoxymethyl)tetrahydro-2H-pyran-2-yl)methyl)phosphoryl) bis(oxy))bis(methylene)bis(2,2-dimethylpropanoate): To a stirred solution of (((((2S,3R,4R,5S,6R)-3-acetamido-4,5-dihydroxy-6-(hydroxymethyl)tetrahydro-2H-pyran-2-yl)methyl)phosphoryl)bis(oxy))bis(methylene)bis(2,2-dimethylpropanoate) (0.12 g, 0.23 mmol, 1.0 equiv) and a catalytic amount of DMAP in dry DCM (12 mL) was added pyridine (1.2 mL) at room temperature. This mixture was stirred at room temperature for 5 minutes and then cooled to 0° C. before acetic anhydride (0.6 mL, 5 equiv.) was added. The resulting solution was warmed to room temperature and then stirred for 16 hours. The reaction mixture was quenched with MeOH (2 mL) at 0° C. and the volatiles were removed in vacuo to give a pale yellow liquid. The product thus obtained was purified by silica gel chromatography, eluting with 70% EtOAc in petroleum ether to give (((((2S,3R,4R,5S,6R)-3-acetamido-4,5-diacetoxy-6-(acetoxymethyl)tetrahydro-2H-pyran-2-yl)methyl)phosphoryl)bis(oxy))bis(methylene)bis(2,2-dimethylpropanoate) as a colorless semi solid (0.12 g, 81%). $^1$H NMR (400 MHz, CDCl$_3$) δ 6.18 (d, J=8.7 Hz, 1H), 5.78-5.62 (m, 4H), 5.06-4.93 (m, 2H), 4.57 (s, 1H), 4.37 (dd, J=12.1, 5.8 Hz, 1H), 4.30-4.22 (m, 2H), 4.01 (d, J=5.2 Hz, 1H), 2.38-2.18 (m, 2H), 2.12 (d, J=1.2 Hz, 6H), 2.10 (s, 3H), 2.01 (s, 3H), 1.25 (d, J=1.3 Hz, 18H). ESI (M+1) 654.0; calc for $C_{27}H_{44}NO_{15}P$ 653.2.

Table of Example Compounds

| Example | Structure | Comments |
|---|---|---|
| 1 | 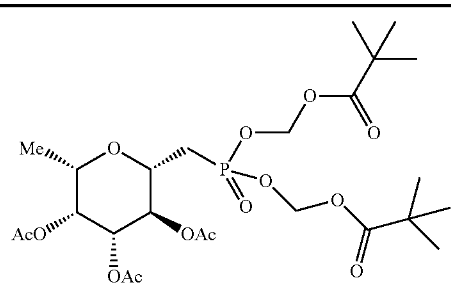 | Beta-L-Fucose Stereochemistry |
| 2 | 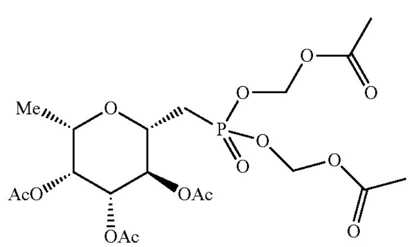 [SMILES: CC(=O)OCOP(=O)(C[C@H]1O[C@@H](C)[C@@H](OC(C)=O)[C@@H](OC(C)=O)[C@@H]1OC(C)=O)OCOC(C)=O] | Beta-L-Fucose Stereochemistry |
| 3 | 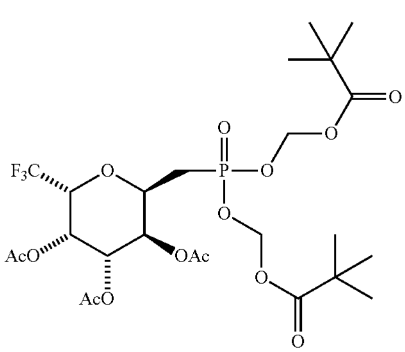 [SMILES: CC(=O)O[C@H]1[C@H](OC(C)=O)[C@H](CP(=O)(OCOC(=O)C(C)(C)C)OCOC(=O)C(C)(C)C)O[C@@H](C(F)(F)F)[C@H]1OC(C)=O] | Alpha-L-Fucose Stereochemistry |
| 4 | | Alpha-D-Mannose Stereochemistry |
| 5 | | Alpha-D-Glucose Stereochemistry |

Cell Surface Protein Fucosylation Assay

The effect of the example compounds on cell surface protein fucosylation was measured in CS-9 CHO cells. A range of amounts of example compound was added to produce various concentrations (100 μM-0.005 uM). These were added to cells grown in batch production CHO cell media in Costar 96-well clear round bottom polypropylene plates and incubated at 37° C. in the presence of 5% $CO_2$. Commercially available standard batch production serum free CHO media such as CD OptiCHO (Invitrogen), Power CHO (Lonza), or ExCell 325 PF CHO (commercially available from Sigma Aldrich) may be used in accordance with the assay. After 3 days, cells were analyzed by fluorescence-activated cell sorting (FACS) using FITC-*Lens culinaris* agglutinin (FITC-LCA, Vector Laboratories Cat#FL-1041) according to the following procedure. After 3 days, 50 uL of FITC-LCA (3 ug/mL) was added to columns 1-11 and plates were incubated for 30 minutes. Plates were then centrifuged briefly (2,000 rpm), and the medium was aspirated away. Cells were washed three times with PBS with 1% BSA, resuspended in the same buffer, and analyzed on the BD LSRii instrument. Cells were simultaneously assayed for viability using propidium iodide.

The following table includes $IC_{50}$ values obtained using the procedures set forth above for the Example compounds described herein.

Table of IC$_{50}$ Values For Example Compounds in Cell Surface Protein Fucosylation Assay

| Example | Structure$^a$ | Cell Surface Protein Fucosylation Assay IC$_{50}$ (μM) | Cell Viability IC$_{50}$ (μM)/max activity at 100 μM |
|---------|---------------|---------|---------|
| 1 | | 21 | >100/94 |
| 2 | | 44 | >100/103 |
| 3 | | 7 | >100/90 |

Assay for Cell Surface Protein High Mannose

The effect of the example compounds on cell surface protein high mannose was measured in CS-9 CHO cells. A range of amounts of example compound was added to produce various concentrations (100 μM-0.005 uM). These were added to cells grown in batch production CHO cell media in Costar 96-well clear round bottom polypropylene plates and incubated at 37° C. in the presence of 5% $CO_2$. Commercially available standard batch production serum free CHO media such as CD OptiCHO (Invitrogen), Power CHO (Lonza), or ExCell 325 PF CHO (commercially available from Sigma Aldrich) may be used in accordance with the assay. After 3 days, cells were analyzed by fluorescence-activated cell sorting (FACS) using FITC-labeled Concanavilin A according to the following procedure. After 3 days, 50 uL of FITC-LCA (3 ug/mL) was added to columns 1-11 and plates were incubated for 30 minutes. Plates were then centrifuged briefly (2,000 rpm), and the medium was aspirated away. Cells were washed three times with PBS with 1% BSA, resuspended in the same buffer, and analyzed on the BD LSRii instrument. Cells were simultaneously assayed for viability using propidium iodide.

Table of IC$_{50}$ Values For Example Compounds in Cell Surface High Mannose Assay

| Example | Structure[a] | Cell Surface High Mannose Assay IC$_{50}$ (μM) | Cell Viability IC$_{50}$ (μM)/max activity at 100 μM |
|---|---|---|---|
| 4 | (structure) | 33.1 | >100/92 |
| 5 | (structure) | 3.4 | >100/88 |

Production Cultures to Generate Antibodies for Glycan Analysis

CHO cells expressing anti-TRAIL IgG1 antibody were seeded into serum-free growth medium in deep 24-well plates via 1:5 dilution. Any medium suitable for growth of CHO cells (i.e. PowerCHO by Lonza or OptiCHO by Invitrogen) can be used. The fucosylation inhibitor Example 1 compound was added to the cultures at inoculation at 5, 10, 20, 40, 80, 160 and 320 uM via 1:1000 dilution of stock solutions in DMSO. The cultures were placed into a shaking incubator (50 mm orbital diameter, 36° C., 5% $CO_2$, 220 rpm). The growth and viability of the cultures were monitored throughout the length of the production assay. The cells were fed with feed medium and an amino acid supplement on days 3, 6 and 8. Cultures were harvested on day 10 via centrifugation and spent medium supernatants were submitted for titer analysis and protein A purification. Glycan analysis of purified antibodies was conducted via the HILIC assay. A graph showing the glycan profile of anti-Trail IgG1 produced in the presence of the Example 1 is shown in FIG. 1.

Maximum inhibition of fucosylation (~10% afucosylation) by Example 1 was observed at 320 uM concentration of the inhibitor.

Figure 2:
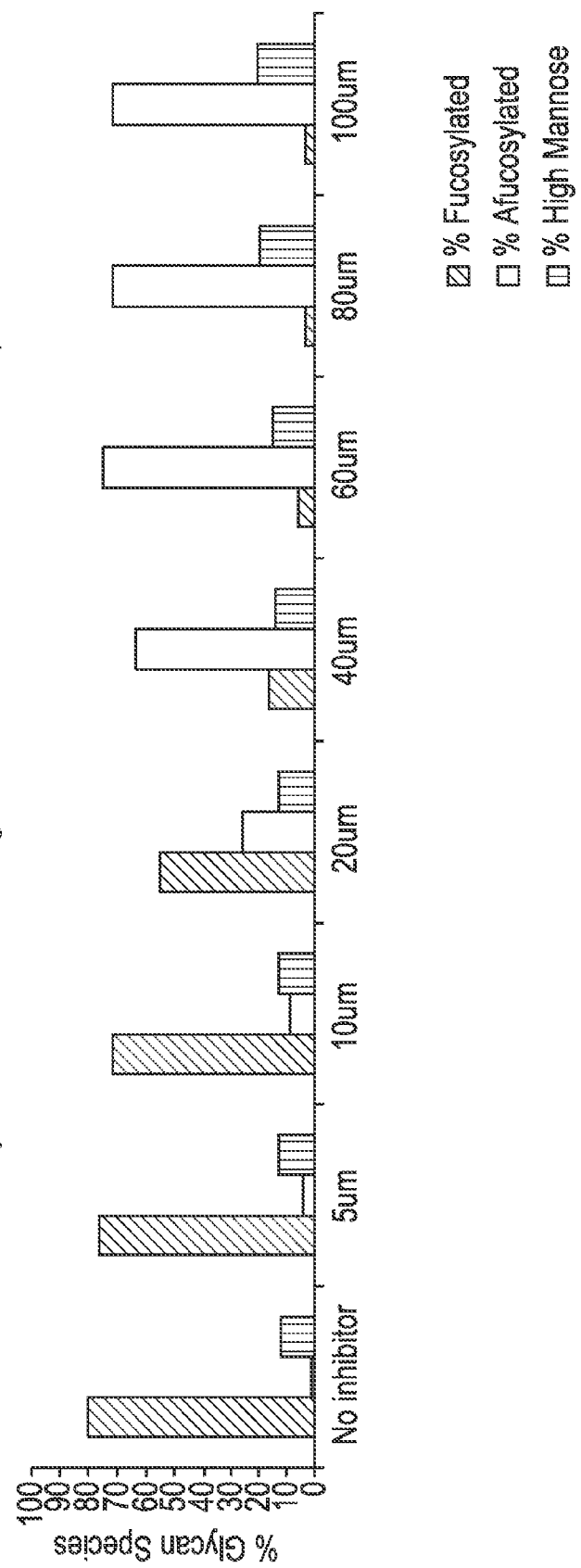
FIG. 2. is a graph comparing the glycan profile of anti-Trail IgG1 produced in the absence of Example 1 and in the presence of the Example 1 at various concentrations added on a daily basis.
Figure 3:
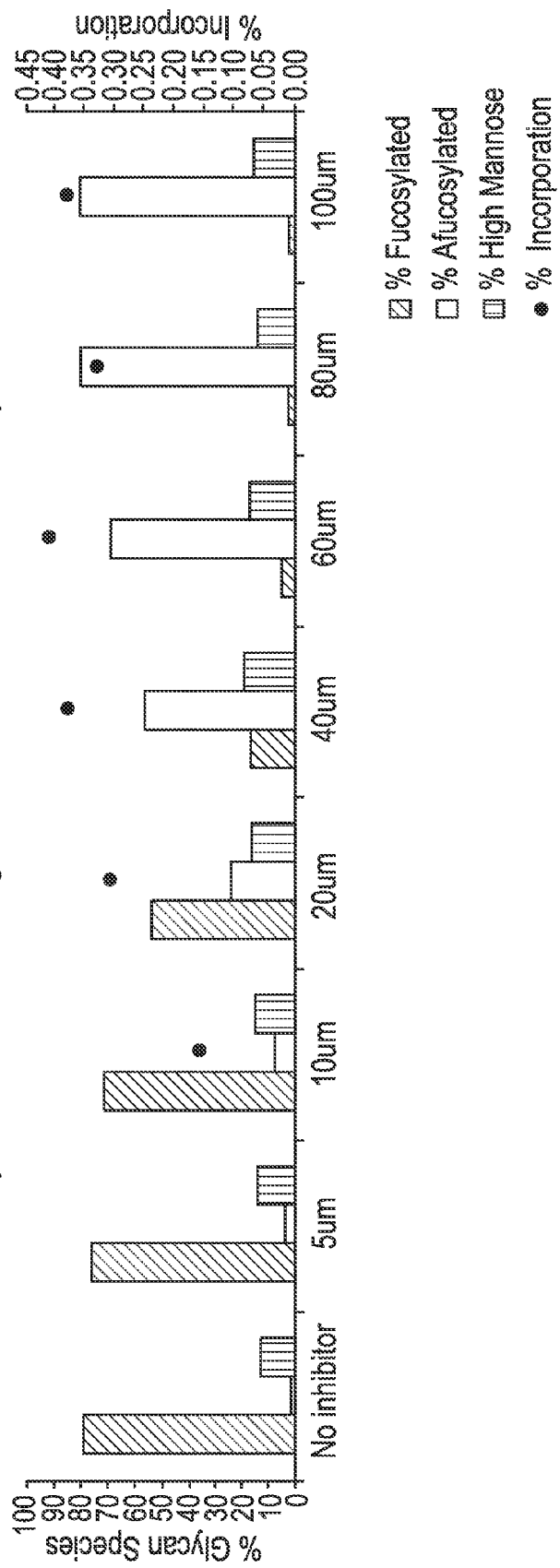
FIG. 3. is a graph comparing the glycan profile of anti-Trail IgG1 produced in the absence of Example 3 and in the presence of the Example 3 at various concentrations added on a daily basis.

To test whether daily doses of the Example 1 fucosylation inhibitor would result in higher inhibition profile, CHO cells expressing anti TRAIL IgG1 antibody were seeded into serum-free growth medium in deep 24-well plates via 1:5 dilution. The fucosylation inhibitor compound Example 1 (FIG. 2) and compound Example 3 (FIG. 3) were added to the cultures on a daily basis at 5, 10, 20, 40, 60, 80, and 100 uM levels via 1:1000 dilution of stock solutions in DMSO. The cultures were placed into a shaking incubator (50 mm orbital diameter, 36° C., 5% $CO_2$, 220 rpm). The growth and viability of cultures were monitored throughout the length of the production assay. Starting on day 3, cells were centrifuged at 1000 rpm for 5 minutes, a fraction of the spent medium was removed and cells were replenished with the equivalent volume of production medium. Cultures were harvested on day 10 via a 10 minute centrifugation at 1000 rpm. Spent medium fractions collected during the course of the experiment were submitted for titer analysis. Spent medium fractions corresponding to select time-points were also purified on protein A. Glycan analysis of the purified antibodies is shown in FIGS. 2 and 3. Addition of Example 3 to cell culture media resulted in some incorporation of part of the inhibitor.

HILIC Analysis

The PNGase F (New England Biolabs) enzymatically-released N-linked glycans from protein-purified anti-TRAIL IgG1 antibody were labeled with 2-aminobenzoic acid (2-AA) and separated by HILIC (hydrophilic interaction liquid chromatography) in-line with a fluorescence detector. The separation was performed using a Waters Acquity UPLC (Waters, Milford, Mass.). In-line MS, using an ion trap mass spectrometer (LTQ; Thermo Scientific, Waltham, Mass.) in positive mode, was incorporated to accommodate mass determination of species. Glycans were injected and bound to the column in high organic conditions and were then eluted with an increasing gradient of an aqueous ammonium formate buffer. Fast separation times were achieved using a 1.7 μM small particle column format (Acquity UPLC BEH Glycan Column, 2.1×100 mm; Waters, Milford, Mass.). Total runtime including column re-equilibration for the MS compatible separation was 30 minutes. Glycan from cells treated with 320 uM Example 1 compound was 64% fucosylated vs. 77% for DMSO control, and contained 13% high mannose vs. 12% for DMSO control. No trace of the inhibitor molecule was detectable in the glycan. Due to limited stability of the Example 1 fucosylation inhibitor in the medium, we expect that significantly greater inhibition of fucosylation will result when the inhibitor is dosed every day.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound of Formula I:

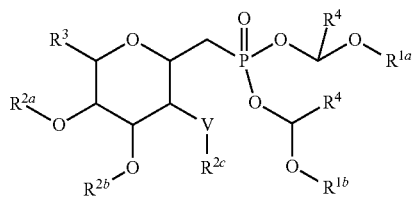

wherein V is O or NH; and further wherein the compound of Formula I is selected from a compound of Formula IA, IB, or IC:

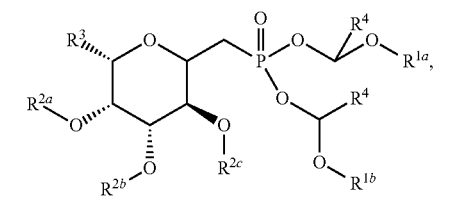

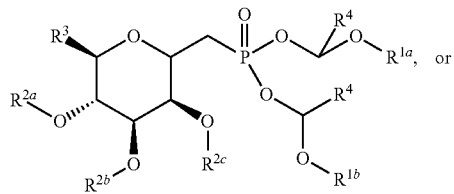

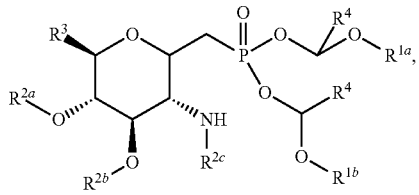

wherein:
$R^{1a}$ and $R^{1b}$ are independently selected from —C(=O)—($C_1$-$C_{10}$ alkyl), or —C(=O)—($C_6$-$C_{10}$ aryl);
$R^{2a}$, $R^{2b}$, and $R^{2c}$ are —C(=O)$CH_3$;
$R^3$ is —$CH_2$O—C(=O)$CH_3$ if the compound of Formula I is a compound of Formula IB;
$R^3$ is selected from ($C_1$-$C_6$)alkyl, perhalo($C_1$-$C_6$)alkyl, halo($C_1$-$C_6$)alkyl, —$CH_2$O—C(=O)—($C_1$-$C_6$ alkyl), or ($C_2$-$C_6$)alkynyl; and
$R^4$ is independently selected from H or —$CH_3$.

2. The compound of claim 1, wherein the compound of Formula I is a compound of Formula IA.

3. The compound of claim 2, wherein the compound of Formula IA is a compound of Formula IA'

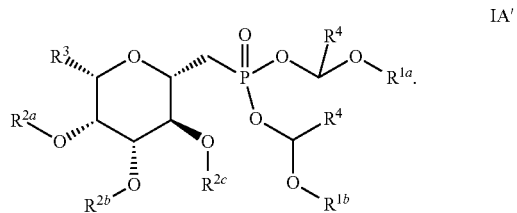

4. The compound of claim 3, wherein $R^3$ is $CH_3$ or $CF_3$.

5. The compound of claim 4, wherein $R^{1a}$ and $R^{1b}$ are —C(=O)—($C_1$-$C_6$ alkyl).

6. The compound of claim 5, wherein $R^{1a}$ and $R^{1b}$ are selected from —C(=O)$CH_3$ or —C(=O)—C($CH_3$)$_3$.

7. The compound of claim 2, wherein the compound is

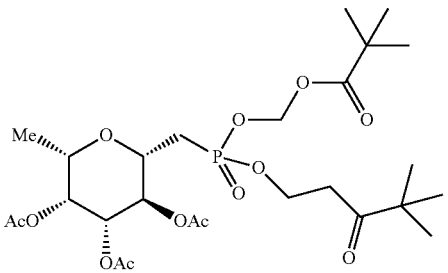 [SMILES: CC(=O)O[C@@H]1[C@H](OC(C)=O)[C@H](C)O[C@H](CP(=O)(OCOC(=O)C(C)(C)C)OCOC(=O)C(C)(C)C)[C@H]1OC(C)=O]

8. The compound of claim 2, wherein the compound is

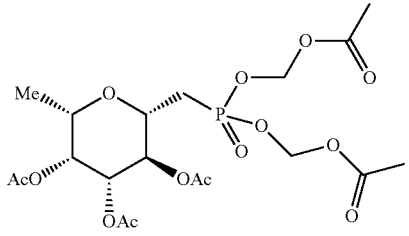 [SMILES: CC(=O)OCOP(=O)(C[C@H]1O[C@@H](C)[C@@H](OC(C)=O)[C@@H](OC(C)=O)[C@@H]1OC(C)=O)OCOC(C)=O]

9. The compound of claim 2, wherein the compound of Formula IA is a compound of Formula IA''

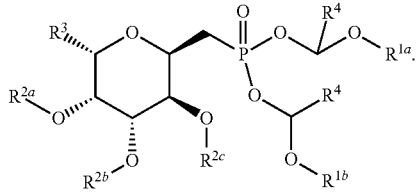

10. The compound of claim 9, wherein $R^3$ is $CF_3$.

11. The compound of claim 10, wherein $R^{1a}$ and $R^{1b}$ are —C(=O)—($C_1$-$C_6$ alkyl).

12. The compound of claim 11, wherein $R^{1a}$ and $R^{1b}$ are selected from —C(=O)$CH_3$ or —C(=O)—C($CH_3$)$_3$.

13. The compound of claim 2, wherein the compound is

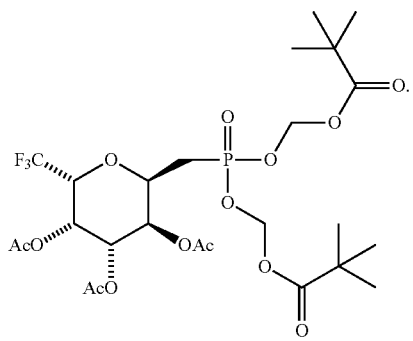 [SMILES: CC(=O)O[C@H]1[C@H](OC(C)=O)[C@H](CP(=O)(OCOC(=O)C(C)(C)C)OCOC(=O)C(C)(C)C)O[C@@H](C(F)(F)F)[C@H]1OC(C)=O]

14. The compound of claim 1, wherein the compound of Formula I is a compound of Formula IB.
15. The compound of claim 14, wherein the compound of Formula IB is a compound of Formula IB'

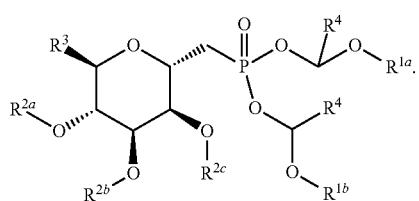

16. The compound of claim 15, wherein $R^{1a}$ and $R^{1b}$ are —C(=O)—($C_1$-$C_6$ alkyl).
17. The compound of claim 16, wherein $R^{1a}$ and $R^{1b}$ are selected from —C(=O)$CH_3$ or —C(=O)—C($CH_3$)$_3$.
18. The compound of claim 14, wherein the compound is

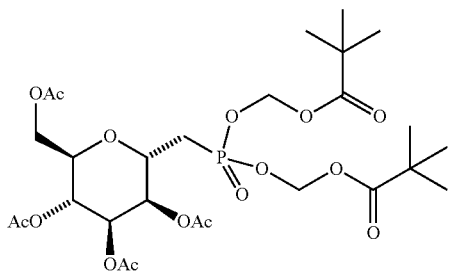

19. The compound of claim 1, wherein the compound of Formula I is a compound of Formula IC.
20. The compound of claim 19, wherein the compound of Formula IC is a compound of Formula IC'

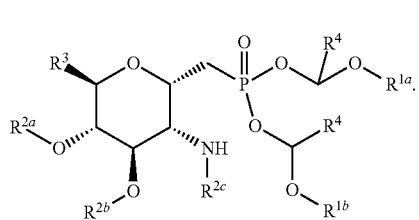

21. The compound of claim 20, wherein $R^3$ is $CH_3$ or $CF_3$.
22. The compound of claim 20, wherein $R^3$ is —$CH_2$O—C(=O)—($C_1$-$C_6$ alkyl).
23. The compound of claim 22, wherein $R^3$ is —$CH_2$O—C(=O)$CH_3$.
24. The compound of claim 20, wherein $R^{1a}$ and $R^{1b}$ are —C(=O)—($C_1$-$C_6$ alkyl).
25. The compound of claim 24, wherein $R^{1a}$ and $R^{1b}$ are selected from —C(=O)$CH_3$ or —C(=O)C($CH_3$)$_3$.
26. The compound of claim 19, wherein the compound is

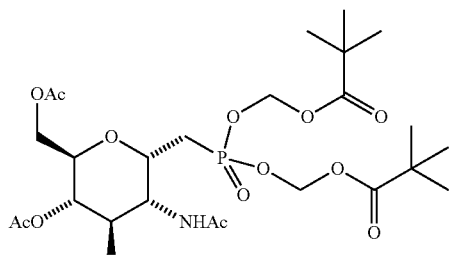

27. The compound of claim 1, wherein $R^{1a}$ and $R^{1b}$ are both —C(=O)—($C_1$-$C_6$ alkyl), and further wherein the —C(=O)—($C_1$-$C_6$ alkyl) is independently selected from —C(=O)$CH_3$, —C(=O)$CH_2CH_3$, —C(=O)$CH_2CH_2CH_3$, —C(=O)$CH_2CH_2CH_2CH_3$, —C(=O)CH($CH_3$)$_2$, —C(=O)C($CH_3$)$_3$, or —C(=O)CH($CH_3$)($CH_2CH_3$).
28. The compound of claim 1, wherein $R^{1a}$ and $R^{1b}$ are both —C(=O)$CH_3$.
29. The compound of claim 1, wherein $R^{1a}$ and $R^{1b}$ are both —C(=O)C($CH_3$)$_3$.
30. The compound of claim 1, wherein $R^{1a}$ and $R^{1b}$ are both —C(=O)—($C_6$-$C_{10}$ aryl) and the —C(=O)—($C_6$-$C_{10}$ aryl) is —C(=O)-phenyl.
31. The compound of claim 1, wherein $R^3$ is selected from ($C_1$-$C_6$)alkyl, perhalo($C_1$-$C_6$)alkyl, or —$CH_2$O—C(=O)—($C_1$-$C_6$ alkyl).
32. The compound of claim 31, wherein $R^3$ is selected from $CF_3$, $CH_3$, or —$CH_2$O—C(=O)$CH_3$.
33. The compound of claim 1, wherein $R^4$ is —H in both instances.
34. The compound of claim 1, wherein $R^4$ is —$CH_3$ in both instances.
35. A method for culturing eukaryotic cells, the method comprising: culturing the cells in a cell culture media, wherein the cell culture media comprises the compound of claim 1.
36. A method for preparing a protein having modified glycan content, the method comprising: culturing eukaryotic host cells in a cell culture media comprising the compound of claim 1, and isolating the protein.
37. The method of claim 35, wherein the compound is added to the cell culture media in a single dose.
38. The method of claim 35, wherein the compound is added to the cell culture media once each day.

* * * * *